US006913911B2

(12) United States Patent
Huisman et al.

(10) Patent No.: US 6,913,911 B2
(45) Date of Patent: *Jul. 5, 2005

(54) TRANSGENIC MICROBIAL POLYHYDROXYALKANOATE PRODUCERS

(75) Inventors: Gjalt W. Huisman, San Carlos, CA (US); Oliver P. Peoples, Arlington, MA (US); Frank A. Skraly, Somerville, MA (US)

(73) Assignee: Metabolix, Inc., Cambridge, MA (US)

( * ) Notice: Subject to any disclaimer, the term of this patent is extended or adjusted under 35 U.S.C. 154(b) by 31 days.

This patent is subject to a terminal disclaimer.

(21) Appl. No.: 10/461,069

(22) Filed: Jun. 13, 2003

(65) Prior Publication Data

US 2003/0228669 A1 Dec. 11, 2003

Related U.S. Application Data

(63) Continuation of application No. 09/375,975, filed on Aug. 17, 1999, now Pat. No. 6,593,116.
(60) Provisional application No. 60/096,852, filed on Aug. 18, 1998.

(51) Int. Cl.$^7$ ............................. C12P 7/62; C12N 1/20; C12N 15/00; C07H 21/04
(52) U.S. Cl. ....................... 435/135; 435/143; 435/146; 435/190; 435/191; 435/193; 435/232; 435/375; 435/252.3; 435/320.1; 435/829; 435/831; 435/877; 536/23.2
(58) Field of Search ................................. 435/135, 143, 435/146, 183, 190, 191, 193, 232, 252.3, 320.1, 375, 829, 831, 877; 536/23.2

(56) References Cited

U.S. PATENT DOCUMENTS

| 4,876,331 A | 10/1989 | Doi ............................. 528/361 |
| 5,000,000 A | 3/1991 | Ingram et al. ............... 435/161 |
| 5,102,797 A | 4/1992 | Tucker et al. ................ 435/473 |
| 5,292,860 A | 3/1994 | Shiotani et al. .............. 528/361 |
| 5,371,002 A | 12/1994 | Dennis et al. ............... 435/142 |
| 5,470,727 A | 11/1995 | Mascarenhas et al. ....... 435/473 |
| 5,512,456 A | 4/1996 | Dennis ........................ 435/69.1 |
| 5,534,432 A | 7/1996 | Peoples et al. ................ 80/298 |
| 5,595,889 A | 1/1997 | Richaud et al. ............. 435/71.2 |
| 6,593,116 B1 * | 7/2003 | Huisman et al. ............. 435/135 |

FOREIGN PATENT DOCUMENTS

| WO | WO 94/21810 | 9/1994 |
| WO | WO 98/04713 | 2/1998 |
| WO | WO 99/14313 | 3/1999 |

OTHER PUBLICATIONS

Abe, et al., "Biosynthesis from gluconate of a random copolyester consisting of 3–hydroxybutyrate and medium–chain–length 3–hydroxyalkanoates by *Pseudomonas* sp. 61–3.," *Int. J. Biol. Macromol.* 16: 115–119 (1994).*

Amos & McInerney, "Composition of poly–β–hydroxyalkanoate from *Syntrophomonas wolfei* grown on unsaturated fatty acid substrates," *Arch. Microbiol.* 155:103–06 (1991).*
Brandl, et al., "Ability of the phototrophic bacterium *Rhodospirillum rubrum* to produce various poly (beta–hydroxyalkanoates): potential sources for biodegradable polyesters," *Int. J. Biol. Macromol.* 11:49–55 (1989).*
Braunegg, et al., "Polyhydroxyalkanoates, biopolyesters from renewable resources: physiological and engineering aspects," *J. Biotech.* 65:127–161 (1998).*
Cevallos, et al., "Genetic and physiological characterization of a *Rhizobium etli* mutant strain unable to synthesize poly–beta–hydroxybutyrate," *J Bacteriol.* 178(6):1646–54 (1996).*
De Lorenzo, et al., "Mini–Tn5 transposon derivatives for insertion mutagenesis, promoter probing, and chromosomal insertion of cloned DNA in gram–negative eubacteria," *J. Bacteriol.* 172(11):6568–6572 (1990).*
De Smet, et al., "Characterization of intracellular inclusions formed by *Pseudomonas oleovorans* during growth in octane," *J. Bacteriol.*, 154: 870–878 (1983).*
Fidler & Dennis, "Polyhydroxyalkanoate production in recombinant *Escherichia coli*," *FEMS Microbiol. Rev.* 103: 231–236 (1992).*
Fukui & Doi, "Cloning and analysis of the poly(3–hydroxybutyrate–co–3–hydroxyhexanoate) biosynthesis genes of *Aeromonas caviae*," *J Bacteriol.* 179(15):4821–30 (1997).*
Hamilton, et al., "New method for generating deletions and gene replacements in *Escherichia coli*," *J. Bacteriol.* 171(9):4617–4622 (1989).*
Hein, et al., "Biosynthesis of poly(4–hydroxybutyric acid) by recombinant strains of *Escherichia coli*," FEMS Microbiol. Lett. 153:411–418 (1997).
Herrero, et al., "Transposon vectors containing non–antibiotic resistance selection markers for cloning and stable chromosomal insertion of foreign genes in gram–negative bacteria," *J. Bacteriol.* 172:6557–6567 (1990).

(Continued)

*Primary Examiner*—Tekchand Saidha
(74) *Attorney, Agent, or Firm*—Pabst Patent Group LLP

(57) ABSTRACT

Transgenic microbial strains are provided which contain the genes required for PHA formation integrated on the chromosome. The strains are advantageous in PHA production processes, because (1) no plasmids need to be maintained, generally obviating the required use of antibiotics or other stabilizing pressures, and (2) no plasmid loss occurs, thereby stabilizing the number of gene copies per cell throughout the fermentation process, resulting in homogeneous PHA product formation throughout the production process. Genes are integrated using standard techniques, preferably transposon mutagenesis. In a preferred embodiment wherein mutiple genes are incorporated, these are incorporated as an operon. Sequences are used to stabilize mRNA, to induce expression as a function of culture conditions (such as phosphate concentration), temperature, and stress, and to aid in selection, through the incorporation of selection markers such as markers conferring antibiotic resistance.

18 Claims, 8 Drawing Sheets

OTHER PUBLICATIONS

Huisman, et. al., "Metabolism of poly(3–hydroxyalkanoates) (PHAs) by *Pseudomonas oleovorans*. Identification and sequences of genes and function of the encoded proteins in the synthesis and degradation of PHA," *J. Biol. Chem.* 266(4):2191–96 (1991).

Hustede & Steinbüchel, "Characterization of the polyhydroxyalkanoate synthase gene locus of *Rhodobacter sphaeroides*," *Biotechnol. Lett.* 15:709–14 (1993).

Hustede et. al., "Cloning of poly(3–hydroxybutyric acid) synthase genes of *Rhodobacter sphaeroides* and *Rhodospirillum rubrum* and heterologous expression in *Alcaligenes eutrophus*," *FEMS Microbiol. Lett* 93: 285–90 (1992).

Kaneko, et al, "Sequence analysis of the genome of the unicellular cyanobacterium *Synechocystis* sp. strain PCC6803. II. Sequence determination of the entire genome and assignment of potential protein–coding regions," *DNA Res.* 3(3):109–36 (1996).

Kato, et al., "Production of a novel copolyester of 3–hydroxybutyric acid with a medium–chain–length 3–hydroxyalkanoic acids by *Pseudomonas* sp. 61-3 from sugars," *Appl. Microbiol. Biotechnol.*, 45:363–70 (1996).

Kidwell, et al., "Regulated expression of *Alcaligenes eutrophus pha* biosynthesis genes in *Escherichia coli*," *Appl. Environ. Microbiol.* 61(4):1391–1398 (1995).

Kim, et al., "Production of poly–β–hydroxybutyrate by by fed–batch culture of recombinant *Escherichia coli*," *Biotechnol. Lett.* 14:811–816 (1992).

Lageveen, et al., "Formation of polyesters by *Pseudomonas oleovorans*: effect of substrates on formation and composition of poly–(R)–3–hydroxyalkanoates and poly–(R)–3–hydroxyalkanoates," *Appl. Environ. Microbiol.* 54:2924–2932 (1988).

Langenbach, et al., "Functional expression of the PHA synthase gene phaC1 from *Pseudomonas aeruginosa* in *Escherichia coli* results in poly(3–hydroxyalkanoate) synthesis," *FEMS Microbiol. Lett.* 150(2):303–309 (1997).

Lawford & Rousseau, "The relationship between enhancement and pet expression in *Escherichia coli*," *Appl. Biochem. Biotechnol.* 57–58:277–292 (1996).

Lee & Chang, "Production of poly(hydroxyalkanoic acid)," *Adv. Biochem. Eng. Biotechnol.* 52:27–58 (1995).

Lee & Lee, "Enhanced production of poly(3–hydroxybutyrate) by filamentation–suppressed recombinant *Escherichia coli* in a defined medium," *J. Environ. Polymer Degrad.* 4: 131–134 (1996).

Lee, "Bacterial polyhydroxyalkanoates," *Biotech. Bioeng.* 49:1–14 (1996).

Lee, "Suppression of filamentation in recombinant *Escherichia coli* by amplified FtsA activity," *Biotechnol. Lett.* 16:1247–1252 (1994).

Lee, et al., "Biosynthesis of copolyesters consisting of 3–hydroxybutyric acid and medium chain length 3–hydroxyalkanoic acids from 1,3–butanediol or from 3–hydroxybutyrate by *Pseudomonas* sp. A33," *Appl. Microbiol. Biotechnol.* 42:901–909 (1995).

Lee, et al., "Comparison of recombinant *Escherichia coli* strains for synthesis and accumulation of poly–(3–hydroxybutyric acid) and morphological changes," *Biotechnol. Bioeng.* 44:1337–1347 (1994).

Lee, et al., "Construction of plasmids, estimation of plasmid stability, and use of stable plasmids for the production of poly(3–hydroxybutyric acid) by recombinant *Escherichia coli*," *J. Biotechnol.* 32(2):203–211 (1994).

Lee, et al., "Production of poly(β–hydroxybutyric acid) by recombinant *Escherichia coli*," *Ann. NY Acad. Sci.* 721:43–53 (1994).

Lee, et al., "Stimulatory effects of amino acids and oleic acid on poly(3–hydroxybutyric acid) synthesis by recombinant *Escherichia coli*," *J. Ferment. Bioeng.* 79: 177–180 (1995).

Lemoigne & Roukhelman, "Fermetation β–hydroxybutyrique caracterisation et evolution des produits de deshydration et de polymerisation de l'acide β–dehydroxybutyrique," *Annales des fermentations* 5:527–36 (1925).

Liebergesell & Steinbuchel, "Cloning and nucleotide sequences of genes relevant for biosynthesis of poly(3–hydroxybutyric acid) in *Chromatium vinosum* strain D," *European J. Biochem.*, 209:135–150 (1992).

Liebergesell & Steinbuchel, "Cloning and molecular analysis of the poly(3–hydroxybutyric acid) biosynthetic genes of *Thiocystis violacea*," *Appl Microbiol Biotechnol.* 38(4):493–501 (1993).

Madison & Huisman, "Metabolic engineering of poly(3–hydroxyalkanoates): from DNA to plastic," *Microbiology and Molecular Biology Reviews* 63:21–53 (1999).

Metcalf, et al., "Conditionally replicative and conjugative plasmids carrying lacZ alpha for cloning, mutagenesis, and allele replacement in bacteria," *Plasmid* 35(1):1–13 (1996).

Miller, *A Short Course in Bacterial Genetics*, Cold Spring Harbor Laboratory Press; Cold Spring Harbor, NY (1992).

Nishimura, et al., "Purification and properties of β–ketothiolase from *Zoogloea ramigera*," *Arch. Microbiol.* 116(1):21–27 (1978).

Panke, et al., "Engineering of Quasi–natural *Pseudomonas putida* strains for toluene metabolism through an ortho–cleavage degradation pathway," *Appl. Environ. Microbiol.* 64(2): 748–751 (1998).

Peoples & Sinskey, "Poly–β–hydroxybutryte (PHB) Biosynthesis in *Alcaligenes eutrophus* H16," *J. Biol. Chem.* 264(26):15298–15303 (1989).

Peoples & Sinskey, "Poly–β–hydroxybutyrate Biosynthesis in *Alcaligenes eutrophus* H16: Characterization of the genes encoding β–ketothiolase and acetoacetyl–CoA reductase," *J. Biol. Chem.* 264: 15293–15297 (1989).

Peoples, et al. "Biosynthetic Thiolase from *Zoogloea ramigera*," *J. Biol. Chem.* 262(1):97–102 (1987).

Peredelchuk & Bennett, "A method for construction of *E. coli* strains with multiple DNA insertions in the chromosome," *Gene* 187(2):231–238 (1997).

Pieper & Steinbüchel, "Identification, cloning and sequence analysis of the poly(3–hydroxyalkanoic acid) synthase gene of the gram–positive bacterium *Rhodococcus ruber*," *FEMS Microbiol Lett.* 75(1):73–9 (1992).

Poirier, et al., "Production of polyhydroxyalkanoates, a family of biodegradable plastics and elastomers, in bacteria and plants," *Biotechnology* 13(2):142–150 (1995).

Preito, et al., "Engineering of stable recombinant bacteria for production of chiral medium–chain–length poly–3–hydroxyalkanoates," *Appl. Environ. Microbiol.* 65:3265–3271 (1999).

Ql, et al., "Metabolic routing towards polyhydroxyalkanoic acid synthesis in recombinant *Escherichia coli* (faoR): inhibition of fatty acid beta–oxidation by acrylic acid," *FEMS Microbiol. Lett.* 167(1):89–94 (1998).

Raibaud, et al., "A technique for integrating any DNA fragment into the chromosome of *Escherichia coli*," *Gene* 29: 231–241 (1984).

Rhie & Dennis, "Role of fadR and atoC(Con) mutations in poly(3–hydroxybutyrate–co 3–hydroxyvalerate) synthesis in recombinant pha+ *Escherichia coli*," *Appl. Environ. Microbiol.* 61(7):2487–2492 (1995).

Saito, et al. "An NADP–linked acetoacetyl CoA reductase from *Zoogloea ramigera*," *Arch. Microbiol.* 114(3):211–17 (1977).

Sambrook, et. al., in *Molecular Cloning, a laboratory manual*, (2nd Ed.), Cold Spring Harbor Laboratory Press: Cold Spring Harbor, NY (1992).

Schembri, et al., "Phosphate concentration regulates transcription of the Acinetobacter polyhydroxybutyric acid (PHB) and synthesis of PHB in *Escherichia coli*," *J. Bacteriol.* 170(12):5837–5847 (1988).

Schubert, et al., "Cloning of the *Alcaligenes eutrophus* genes for synthesis of poly–β–hydroxybutyri acid (PHB) and synthesis of PHB in *Escherichia coli*," *J. Bacteriol.* 170: 5837–5847 (1988).

Sim, et al., "PHA synthese activity controls the molecular weight and polydispersity of polyhydroxybutyrate in vivo," *Nature Biotech.* 15:63–67 (1997).

Slater, et al., "Cloning and expression in *Escherichia coli* of the *Alcaligenes eutrophus* H16 poly–β–hydroxybutyrate biosynthetic pathway," *J. Bacteriol.* 170: 4431–4436 (1988).

Slater, et al., "Production of poly–(3–hydroxybutyrate–co–3–hydroxyvalerate) in a recombinant *Escherichia coli* strain," *Appl. Environ. Microbiol.* 58(4):1089–1094 (1992).

Steinbüchel & Valentin, "Diversity of bacterial polyhydroxyalkanoic acids," *FEMS Microbiol. Lett.* 128:219–28 (1995).

Steinbüchel & Wiese, "A *Psuedomonas* strain accumulating polyesters of 3–hydroxybutyric acid and medium–chain–length 3–hydroxyalkanoic acids," *Appl. Microbiol. Biotechnol.* 37:691–97 (1992).

Steinbüchel, et al., "Molecular basis for biosynthesis and accumulation of polyhydroxyalkanoic acids in bacteria," *FEMS Microbiol Rev.* 9(2–4):217–30 (1992).

Timm & Steinbüchel, "Cloning and molecular analysis of the poly(3–hydroxyalkanoic acid) gene locus of *Pseudomonas aeruginosa* PAO1," *Eur J Biochem.* 209(1):15–30 (1992).

Tombolini, et al., "Poly–beta–hydroxybutyrate (PHB) biosynthetic genes in *Rhizobium meliloti* 41," *Microbiology.* 141 (Pt 10):2553–9 (1995).

Ueda, et al., "Molecular analysis of the poly(3–hdyroxyalkanoate) synthase gene from a methylotrophic bacterium, *Paracoccus denitrificans*," *J Bacteriol.* 178(3):774–9 (1996).

Valentin & Dennis, "Production of poly(3–hydroxybutyrate–co–4,–hydroxybutyrate) in recombinant *Escherichia coli* grown on glucose," *J. Biotechnol.* 58:33–38 (1997).

Valentin, et al., "Identification of 4–hydroxyhexanoic acid as a new constituent of biosynthetic polyhydroxyalkanoic acids from bacteria," *Appl. Microbiol. Biotechnol.* 40:710–16 (1994).

Valentin, et al., "Identification of 4–hydroxyvaleric acid as a constituent of biosynthetic polyhydroxyalkanoic acids from bacteria," *Appl. Microbiol. Biotechnol.* 36: 507–14 (1992).

Valentin, et al., "Identification of 5–hydroxyhexanoic acid, 4–hydroxyaheptanoic acid and 4–hydroxyoctanoic acid as new constituents of bacterial polyhydroxyalkanoic acids," *Appl. Microbiol. Biotechnol.* 46:261–67 (1996).

Valentin, et al., "Cloning and characterization of the Methylobacterium extorquens polyhydroxyalkanoic–acid–synthase structural gene," *Appl Microbiol Biotechnol.* 39(3):309–17 (1993).

Valentin, et al., "Metabolic pathway for biosynthesis of poly(3–hydroxybutyrate–co–4–hydroxybutyrate) from 4–hydroxybutyrate by *Alcaligenes eutrophus*," *Eur. J. Biochem.* 227:43–60 (1995).

Wallen & Rohwedder, "Poly–β–hydroxyalkanoate from activated sludge," *Environ. Sci. Technol.* 8:576–79 (1974).

Wang & Lee, "High cell density culture of metabolically engineered *Escherichia coli* for the production of poly(3–hydroxybutyrate) in a defined medium," *Biotechnol. Bioeng.* 58(2–3):325–328 (1998).

Wang & Lee, "Production of poly(3–hydroxybutyrate) by fed–batch culture of filamentation suppressed recombinant *Escherichia coli*," *Appl. Environ. Microbiol.* 63(12): 4765–4769 (1997).

Williams & Peoples, "Biodegradable plastics from plants," *CHEMTECH* 26:38–44 (1996).

Yabutani, et al., "Analysis of beta–ketothiolase and acetoacetyl–CoA reductase genes of a methylotrophic bacterium, *Paracoccus denitrificans*, and their expression in *Escherichia coli*," *FEMS Microbiol Lett.* 133(1–2):85–90 (1995).

Yim, et al., "Synthesis of Poly–(3–hydroxybutyrate–co–3–hydroxyvalerate) by recombinant *Escherichia coli*," *Biotech. Bioengineering* 49:495–503 (1996).

Zhang, et al., "Production of polyhydroxyalkanoates in sucrose–utilizing recombinant *Escherichia coli* and *Klebsiella* strains," *Appl. Environ. Microbiol.* 60:1198–1205 (1994).

* cited by examiner

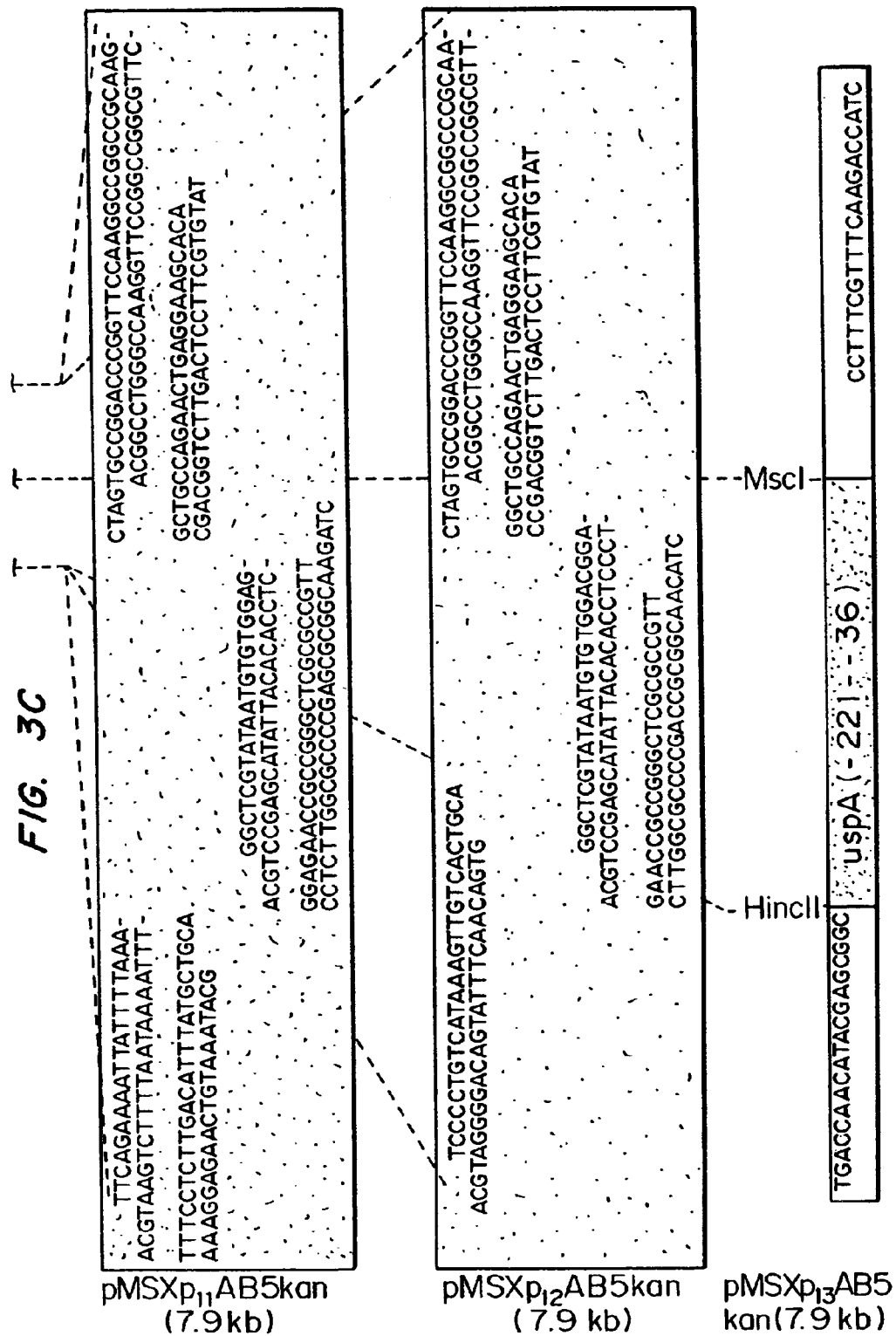

SEQUENCE LISTING

<160> NUMBER OF SEQ ID NOS: 39

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
aagcttccca gcccgctaat gagcgggctt tttttttgaac aaaagcatgc          50

<210> SEQ ID NO 2
<211> LENGTH: 71
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gtctacgtac cccaggcttt acatttatgc ttccggctcg tatgttgtgt ggaattgtga     60
gcggttcgga c                                                           71

<210> SEQ ID NO 3
<211> LENGTH: 48
<212> TYPE: DNA

```
<213> ORGANISM: Artificial Sequence
<220> FEATURE:
<223> OTHER INFORMATION: Description of Artificial Sequence:
      oligonucleotide

<400> SEQUENCE: 3
agcttcccag cccgctaatg agcgggcttt tttttgaaca aaagctgc                48

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
cttttgttca aaaaaagcc cgctcattag cgggctggga                          40

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ggctcgtata atgtgtggag ggagaaccgc cgggctcgcg ccgtt                   45

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ctagaacggc gcgagcccgg cggttctccc tccacacatt atacgagcct gca          53

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ttcagaaaat tattttaaat ttcctcttga catttatgct gca                     43

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gcataaatgt caagaggaaa tttaaaataa ttttctgaat gca                     43

<210> SEQ ID NO 9
<211> LENGTH: 58
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 9
ctagtgccgg acccggttcc aaggccggcc gcaaggctgc cagaactgag gaagcaca        58

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tatgtgcttc ctcagttctg gcagccttgc ggccggcctt ggaaccgggt ccggca          56

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tcccctgtca taaagttgtc actgca                                           26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
gtgacaactt tatgacaggg gatgca                                           26

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
tgaccaacat acgagcggc                                                   19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
ctaccagaac tttgctttcc                                                  20

<210> SEQ ID NO 15
<211> LENGTH: 36
<212> TYPE: DNA
<213> ORGANISM: Artificial Sequence
<220> FEATURE:
```

```
<223> OTHER INFORMATION: Description of Artificial Sequence:
      oligonucleotide

<400> SEQUENCE: 15
tgcatgcgat atcaattgtc cagccagaaa gtgagg                              36

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
atttattcaa caaagccgcc                                                20

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
cccagcccgc taatgagcgg gcttttttt gaacaaaa                             38

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
tacgtatttt gttcaaaaaa aagcccgctc attagcgggc tggg                     44

<210> SEQ ID NO 19
<211> LENGTH: 63
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
tacgtacccc aggctttaca tttatgcttc cggctcgtat gttgtgtgga attgtgagcg    60
gtt                                                                 63

<210> SEQ ID NO 20
<211> LENGTH: 61
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ttcgaaccgc tcacaattcc acacaacata cgagccggaa gcataaatgt aaagcctggg    60
g                                                                   61

<210> SEQ ID NO 21
<211> LENGTH: 14
```

```
<212> TYPE: DNA
<213> ORGANISM: Pseudomonas oleovorans

<400> SEQUENCE: 21
aggaggtttt tatg                                                        14

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 22
ggaattcagg aggttttatg gcgaccggca aaggcgcggc ag                         42

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 23
gctctagaag ctttcatgcc ttggctttga cgtatcgc                              38

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 24
ggaattcagg aggttttatg agtaacaaga acaacgatga gc                         42

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 25
gctctagaag ctttcaacgc tcgtgaacgt aggtgccc                              38

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 26
ggaattcagg aggttttatg agccaaccat cttatggccc gc                         42

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 27
gctctagaag ctttcatgcg gcgtcctcct ctgttggg                              38
```

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 28
ggaattcagg aggttttatg aggccagaaa tcgctgtact tg                    42

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 29
gctctagaag ctttcagatg gcaaatgcat gctgcccc                        38

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 30
aggagctcag gaggttttat gagcgcacaa tccctggaag tag                   43

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 31
gctctagaag cttttaaggc agcttgacca cggcttcc                        38

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 32
ggaattcagg aggttttatg acgcgtgaag tggtagtggt aag                   43

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 33
gctctagaag ctttcagata cgctcgaaga tggcggc                         37

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: primer -continued

<400> SEQUENCE: 34
ggaattcagg aggttttatg atcctcaccc cggaacaagt tg                           42

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 35
gctctagaag ctttcagggc actaccttca tcgttggc                               38

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 36
gctctagaag ctttcaggca gccgtcgtct tctttgcc                               38

<210> SEQ ID NO 37
<211> LENGTH: 39
<212> TYPE: DNA
<213> ORGANISM: Aeromonas caviae

<400> SEQUENCE: 37
agaattcagg aggacgccgc atgagcgcac aatccctgg                              39

<210> SEQ ID NO 38
<211> LENGTH: 29
<212> TYPE: DNA
<213> ORGANISM: Aeromonas caviae

<400> SEQUENCE: 38
ttcctgcagc tcaaggcagc ttgaccacg                                         29

<210> SEQ ID NO 39
<211> LENGTH: 1680
<212> TYPE: DNA
<213> ORGANISM: Pseudomonas oleovorans

<400> SEQUENCE: 39
atgagtaaca agaacaacga tgagctgcag cggcaggcct cggaaaacac cctggggctg      60
aacccggtca tcggtatccg ccgcaaagac ctgttgagct cggcacgcac cgtgctgcgc    120
caggccgtgc gccaaccgct gcacagcgcc aagcatgtgg cccactttgg cctggagctg    180
aagaacgtgc tgctgggcaa gtccagcctt gccccggaaa gcgacgaccg tcgcttcaat    240
gacccggcat ggagcaacaa cccactttac cgccgctacc tgcaaaccta tctggcctgg    300
cgcaaggagc tgcaggactg gatcggcaac agcgacctgt cgccccagga catcagccgc    360
ggccagttcg tcatcaacct gatgaccgaa gccatggctc cgaccaacac cctgtccaac    420
ccggcagcag tcaaacgctt cttcgaaacc ggcggcaaga gcctgctcga tggcctgtcc    480
aacctggcca aggacctggt caacaacggt ggcatgccca ccaggtgaa catggacgcc     540 ttcgaggtgg gcaagaacct gggcaccagt gaaggcgccg tggtgtaccg caacgatgtg    600
ctggagctga tccagtacaa ccccatcacc gagcaggtgc atgcccgccc gctgctggtg    660

-continued

```
gtgccgccgc agatcaacaa gttctacgta ttcgacctga gcccggaaaa gagcctggca      720
cgctactgcc tgcgctcgca gcagcagacc ttcatcatca gctggcgcaa cccgaccaaa      780
gcccagcgcg aatggggcct gtccacctac atcgacgcgc tcaaggaggc ggtcgacgcg      840
gtgctggcga ttaccggcag caaggacctg aacatgctcg gtgcctgctc cggcggcatc      900
acctgcacgg cattggtcgg ccactatgcc gccctcggcg aaaacaaggt caatgccctg      960
accctgctgg tcagcgtgct ggacaccacc atggacaacc aggtcgccct gttcgtcgac     1020
gagcagactt tggaggccgc caagcgccac tcctaccagg ccggtgtgct cgaaggcagc     1080
gagatggcca aggtgttcgc ctggatgcgc cccaacgacc tgatctggaa ctactgggtc     1140
aacaactacc tgctcggcaa cgagccgccg gtgttcgaca tcctgttctg gaacaacgac     1200 accacgcgc tgccggccgc cttccacggc gacctgatcg aaatgttcaa gagcaacccg     1260 ctgaccgcc cggacgccct ggaggtttgc ggcactccga tcgacctgaa acaggtcaaa     1320
tgcgacatct acagccttgc cggcaccaac gaccacatca cccgtggca gtcatgctac     1380 cgctcggcgc acctgttcgg cggcaagatc gagttcgtgc tgtccaacag cggccacatc     1440
cagagcatcc tcaacccgcc aggcaacccc aaggcgcgct tcatgaccgg tgccgatcgc     1500
ccgggtgacc cggtggcctg gcaggaaaac gccaccaagc atgccgactc ctggtggctg     1560
cactggcaaa gctggctggg cgagcgtgcc ggcgagctga aaaaggcgcc gacccgcctg     1620
ggcaaccgtg cctatgccgc tggcgaggca tccccgggca cctacgttca cgagcgttga     1680
```

TRANSGENIC MICROBIAL POLYHYDROXYALKANOATE PRODUCERS

CROSS-REFERENCE TO RELATED APPLICATIONS

This is a continuation of U.S. Ser. No. 09/375,975 filed Aug. 17, 1999, U.S. Pat. No. 6,593,116, which claims priority to U.S. provisional application Ser. No. 60/096,852, filed Aug. 18, 1998, the teachings of which are incorporated herein.

BACKGROUND OF THE INVENTION

The present invention is generally in the field of biosynthesis of poly(3-hydroxyalkanoates), and more particularly to improved microbial strains useful in commercial production of polyhydroxyalkanoates.

Poly(3-hydroxyalkanoates) (PHAs) are biological polyesters synthesized by a broad range of bacteria. These polymers are biodegradable and biocompatible thermoplastic materials, produced from renewable resources, with a broad range of industrial and biomedical applications (Williams & Peoples, CHEMTECH 26:38–44 (1996)). PHA biopolymers have emerged from what was originally considered to be a single homopolymer, poly-3-hydroxybutyrate (PHB) into a broad class of polyesters with different monomer compositions and a wide range of physical properties. About 100 different monomers have been incorporated into the PHA polymers (Steinbuchel & Valentin, FEMS Microbiol. Lett. 128:219–28 (1995)).

It has been useful to divide the PHAs into two groups according to the length of their side chains and their biosynthetic pathways. Those with short side chains, such as PHB, a homopolymer of R-3-hydroxybutyric acid units, are crystalline thermoplastics, whereas PHAs with long side chains are more elastomeric. The former have been known for about seventy years (Lemoigne & Roukhelman, 1925), whereas the latter materials were discovered relatively recently (deSmet et al., J. Bacteriol. 154:870–78 (1983)). Before this designation, however, PHAs of microbial origin containing both (R)-3-hydroxybutyric acid units and longer side chain (R)-3-hydroxyacid units from $C_5$ to $C_{16}$ had been identified (Wallen & Rohweder, Environ. Sci. Technol. 8:576–79 (1974)). A number of bacteria which produce copolymers of (R)-3-hydroxybutyric acid and one or more long side chain hydroxyacid units containing from five to sixteen carbon atoms have been identified (Steinbuchel & Wiese, Appl. Microbiol. Biotechnol. 37:691–97 (1992); Valentin et al., Appl. Microbiol. Biotechnol. 36:507–14 (1992); Valentin et al., Appl. Microbiol. Biotechnol. 40:710–16 (1994); Abe et al., Int. J. Biol. Macromol. 16:115–19 (1994); Lee et al., Appl. Microbiol. Biotechnol. 42:901–09 (1995); Kato et al., Appl. Microbiol. Biotechnol. 45:363–70 (1996); Valentin et al., Appl. Microbiol. Biotechnol. 46:261–67 (1996); U.S. Pat. No. 4,876,331 to Doi). A combination of the two biosynthetic pathways outlined described above provide the hydroxyacid monomers. These copolymers can be referred to as PHB-co-HX (where X is a 3-hydroxyalkanoate or alkanoate or alkenoate of 6 or more carbons). A useful example of specific two-component copolymers is PHB-co-3-hydroxyhexanoate (PHB-co-3HH) (Brandl et al., Int. J. Biol. Macromol. 11:49–55 (1989); Amos & Mclnerey, Arch. Microbiol. 155:103–06 (1991); U.S. Pat. No. 5,292,860 to Shiotani et al.).

PHA production by many of the microorganisms in these references is not commercially useful because of the complexity of the growth medium, the lengthy fermentation processes, or the difficulty of down-stream processing of the particular bacterial strain. Genetically engineered PHA production systems with fast growing organisms such as Escherichia coli have been developed. Genetic engineering also allows for the improvement of wild type PHA production microbes to improve the production of specific copolymers or to introduce the capability to produce different PHA polymers by adding PHA biosynthetic enzymes having different substrate-specificity or even kinetic properties to the natural system. Examples of these types of systems are described in Steinbuchel & Valentin, FEMS Microbiol. Lett. 128:219–28 (1995). PCT WO 98/04713 describes methods for controlling the molecular weight using genetic engineering to control the level of the PHA synthase enzyme. Commercially useful strains, including Alcaligenes eutrophus (renamed as Ralstonia eutropha), Alcaligenes latus, Azotobacter vinlandii, and Pseudomonads, for producing PHAs are disclosed in Lee, Biotechnology & Bioengineering 49:1–14 (1996) and Braunegg et al., (1998), J. Biotechnology 65: 127–161.

The development of recombinant PHA production strains has followed two parallel paths. In one case, the strains have been developed to produce copolymers, a number of which have been produced in recombinant E. coli. These copolymers include poly(3-hydroxybutyrate-co-3-hydroxyvalerate) (PHBV), poly(3-hydroxybutyrate-co-4-hydroxybutyrate) (P3HB-co-4HB), poly(4-hydroxybutyrate) (P4HB) and long side chain PHAs comprising 3-hydroxyoctanoate units (Madison and Huisman, 1999. Strains of E. coli containing the phb genes on a plasmid have been developed to produce P(3HB-3HV) (Slater, et al., Appl. Environ. Microbiol. 58:1089–94 (1992); Fidler & Dennis, FEMS Microbiol. Rev. 103:231–36 (1992); Rhie & Dennis, Appl. Environ. Micobiol. 61:2487–92 (1995); Zhang, H. et al., Appl. Environ. Microbiol. 60:1198–205 (1994)). The production of P(4HB) and P(3HB-4HB) in E. coli is achieved by introducing genes from a metabolically unrelated pathway into a P(3HB) producer (Hein, et al., FEMS Microbiol. Lett. 153:411–18 (1997); Valentin & Dennis, J. Biotechnol. 58:33–38 (1997)). E. coli also has been engineered to produce medium short chain polyhydroxyalkanoates (msc-PHAs) by introducing the phaC1 and phaC2 gene of P. aeruginosa in a fadB::kan mutant (Langenbach, et al., FEMS Microbiol. Lett. 150:303–09 (1997); Qi, et al., FEMS Microbiol. Lett. 157:155–62 (1997)).

Although studies demonstrated that expression of the A. eutrophus PHB biosynthetic genes encoding PHB polymerase, -ketothiolase, and acetoacetyl-CoA reductase in E. coli resulted in the production of PHB (Slater, et al., J. Bacteriol. 170:4431–36 (1988); Peoples & Sinskey, J. Biol. Chem. 264:15298–303 (1989); Schubert, et al., J. Bacteriol. 170:5837–47 (1988)), these results were obtained using basic cloning plasmid vectors and the systems are unsuitable for commercial production since these strains lacked the ability to accumulate levels equivalent to the natural producers in industrial media.

For commercial production, these strains have to be made suitable for large scale fermentation in low cost industrial medium. The first report of recombinant P(3HB) production experiments in fed-batch cultures used an expensive complex medium, producing P(3HB) to 90 g/L in 42 hours using a ph-stat controlled system (Kim, et al., Biotechnol. Lett. 14:811–16 (1992)). Using stabilized plasmids derived from either medium- or high-copy-number plasmids, it was shown that E. coli XL1-Blue with the latter type plasmid is required for substantial P(3HB) accumulation (Lee, et al., Ann. N.Y. Acad. Sci. 721:43–53 (1994)). In a fed-batch fermentation on 2% glucose/LB medium, this strain produced 81% P(3HB) at a productivity of 2.1 g/L-hr (Lee, et al., *J. Biotechnol.* 32:203–11 (1994)). The P(3HB) productivity was reduced to 0.46 g/L-hr in minimal medium, but could be recovered by the addition of complex nitrogen sources such as yeast extract, tryptone, casamino acids, and collagen hydrolysate (Lee & Chang, *Adv. Biochem. Eng. Biotechnol.* 52:27–58 (1995); Lee, et al., *J. Ferment. Bioeng.* 79:177–80 (1995)).

Although recombinant *E. coli* XL1-blue is able to synthesize substantial levels of P(3HB), growth is impaired by dramatic filamentation of the cells, especially in defined medium (Lee, et al., *Biotechnol. Bioeng.* 44:1337–47 (1994); Lee, *Biotechnol. Lett.* 16:1247–52 (1994); Wang & Lee, *Appl. Environ. Microbiol.* 63:4765–69 (1997)). By overexpression of FtsZ in this strain, biomass production was improved by 20% and P(3HB) levels were doubled (Lee & Lee, *J. Environ. Polymer Degrad.* 4:131–34 (1996)). This recombinant strain produced 104 g/L P(3HB) in defined medium corresponding to 70% of the cell dry weight. The volumetric productivity of 2 g/L-hr, however, is lower than achievable with *R. eutropha*. Furthermore, about 15% of the cells lost their ability to produce PHB by the end of the fermentation (Wang & Lee, *Biotechnol. Bioeng.* 58:325–28 (1998)).

Recombinant *E. coli* P(3HB-3HV) producers reportedly are unable to grow to a high density and therefore are unsuited for commercial processes (Yim, et al., *Biotechnol. Bioeng.* 49:495–503 (1996)). In an attempt to improve P(3HB-3HV) production in a recombinant strain, four *E. coli* strains (XL1-Blue, JM109, HB101, and DH5α) were tested by Yim et al. All four recombinant *E. coli* strains synthesized P(3HB-3HV) when grown on glucose and propionate with HV fractions of 7% (Yim, et al., *Biotechnol. Bioeng.* 49:495–503 (1996)). Unlike other strains studied (Slater, et al., *Appl. Environ. Microbiol.* 58:1089–94 (1992)), recombinant XL1-Blue incorporates less than 10% HV when the propionic acid concentration is varied between 0 and 80 mM. HV incorporation and PHA formation were increased by pre-growing cells on acetate followed by glucose/propionate addition at a cell density of around $10^8$ cells per ml. Oleate supplementation also stimulated HV incorporation. This recombinant XL1-Blue when pregrown on acetate and with oleate supplementation reached a cell density of 8 g/L, 75% of which was P(3HB-3HV) with an HV fraction of 0.16 (Yim, et al., *Biotechnol. Bioeng.* 49:495–503 (1996)).

One of the challenges of producing P(3HB) in recombinant organisms is the stable and constant expression of the phb genes during fermentation. Often P(3HB) production by recombinant organisms is hampered by the loss of plasmid from the majority of the bacterial population. Such stability problems may be attributed to the metabolic load exerted by the need to replicate the plasmid and synthesize P(3HB), which diverts acetyl-CoA to P(3HB) rather than to biomass. In addition, plasmid copy numbers often decrease upon continued fermentation because only a few copies provide the required antibiotic resistance or prevent cell death by maintaining parB. For these reasons, a runaway plasmid was designed to suppress the copy number of the plasmid at 30 C. and induce plasmid replication by shifting the temperature to 38 C. (Kidwell, et al., *Appl. Environ. Microbiol.* 61:1391–98 (1995)). Using this system, P(3HB) was produced to about 43% of the cell dry weight within 15 hours after induction with a volumetric production of 1 gram P(3HB) per liter per hour. Although this productivity is of the same order of magnitude as natural P(3HB) producers, strains harboring these parB-stabilized runaway replicons still lost the capacity to accumulate P(3HB) during prolonged fermentations.

While the instability of the phb genes in high cell-density fermentations affects the PHA cost by decreasing the cellular P(3HB) yields, the cost of the feedstock also contributes to the comparatively high price of PHAs. The most common substrate used for P(3HB) production is glucose. Consequently, *E. coli* and *Klebsiella* strains have been examined for P(3HB) formation on molasses, which cost 33–50% less than glucose (Zhang, et al., *Appl. Environ. Microbiol.* 60:1198–1205 (1994)). The main carbon source in molasses is sucrose. Recombinant *E. coli* and *K. aerogenes* strains carrying the phb locus on a plasmid grown in minimal medium with 6% sugarcane molasses accumulated P(3HB) to approximately 3 g/L corresponding to 45% of the cell dry weight. When the *K. aerogenes* was grown fed-batch in a 10 L fermenter on molasses as the sole carbon source, P(3HB) was accumulated to 70% its cell dry weight, which corresponded to 24 g/L. Although the phb plasmid in *K. aerogenes* was unstable, this strain shows promise as a P(3HB) producer on molasses, especially since fadR mutants incorporate 3HV up to 55% in the presence of propionate (Zhang, et al., *Appl. Environ. Microbiol.* 60:1198–1205 (1994)).

U.S. Pat. No. 5,334,520 to Dennis discloses the production of PHB in *E. coli* transformed with a plasmid containing the phbCAB genes. A rec$^-$, lac$^+$ *E. coli* strain was grown on whey and reportedly accumulates PHB to 85% of its cell dry weight. U.S. Pat. No. 5,371,002 to Dennis et al. discloses methods to produce PHA in recombinant *E. coli* using a high copy number plasmid vector with phb genes in a host that expresses the acetate genes either by induction, constitutively, or from a plasmid. U.S. Pat. No. 5,512,456 to Dennis discloses a method for production and recovery of PHB from transformed *E. coli* strains. These *E. coli* strains are equipped with a vector containing the phb genes and a vector containing a lysozyme gene. High copy number plasmids or runaway replicons are used to improve productivity. The vectors are stabilized by parB or by supF/dnaB (am). Using such strains, a productivity of 1.7 g/L-hr was obtained corresponding to 46 g/L PHB in 25 hrs, after which the plasmid was increasingly lost by the microbial population. PCT WO94/21810 discloses the production of PHB in recombinant strains of *E. coli* and *Klebsiella aerogenes* with sucrose as a carbon source. PCT WO 95/21257 discloses the improved production of PHB in transformed prokaryotic hosts. Improvements in the transcription regulating sequences and ribosome binding site improve PHB formation by the plasmid based phb genes. The plasmid is stabilized by the parB locus. PHB production by this construct is doubled by including the 361 nucleotides that are found upstream of phbC in *R. eutropha* instead of only 78 nucleotides. It is generally believed that PHB production by recombinant microorganisms requires high levels of expression using stabilized plasmids. Since plasmids are available in the cell in multiple copies, ranging from one to several hundreds, the use of plasmids ensured the presence of multiple copies of the genes of interest. Since plasmids may be lost, stabilization functions are introduced. Such systems, which are described above, have been tested for PHB production, and the utility of these systems in industrial fermentation processes has been investigated. However, overall PHB yield is still affected by loss of phb genes.

It is therefore an object of the present invention to provide recombinant microorganisms strains useful in industrial fermentation processes which can accumulate commercially significant levels of PHB while providing stable and constant expression of the phb genes during fermentation.

It is another object of the present invention to provide transgenic microbial strains for enhanced production of poly(3-hydroxyalkanoates).

It is another object of the present invention to provide transgenic microbial strains which yield stable and constant expression of the phb genes during fermentation and accumulate commercially significant levels of PHB, and methods of use thereof.

SUMMARY OF THE INVENTION

Transgenic microbial strains are provided which contain the genes required for PHA formation integrated on the chromosome. The strains are advantageous in PHA production processes, because (1) no plasmids need to be maintained, generally obviating the required use of antibiotics or other stabilizing pressures, and (2) no plasmid loss occurs, thereby stabilizing the number of gene copies per cell throughout the fermentation process, resulting in homogeneous PHA product formation throughout the production process. Genes are integrated using standard techniques, preferably transposon mutagenesis. In a preferred embodiment wherein mutiple genes are incorporated, these are incorporated as an operon. Sequences are used to stabilize mRNA, to induce expression as a function of culture conditions (such as phosphate concentration), temperature, and stress, and to aid in selection, through the incorporation of selection markers such as markers conferring antibiotic resistance.

BRIEF DESCRIPTION OF THE DRAWINGS

FIGS. 3A–3C are a diagram showing the construction of pMUXAB$_5$cat, pMUXTp$_1$AB$_5$kan, pMUXTp$_{11}$AB$_5$kan, pMUXTp$_{12}$AB$_5$ kan, and pMUXTp$_{13}$AB$_5$kan (SEQ ID NO: 3–14).

DETAILED DESCRIPTION OF THE INVENTION

Figure 1A:
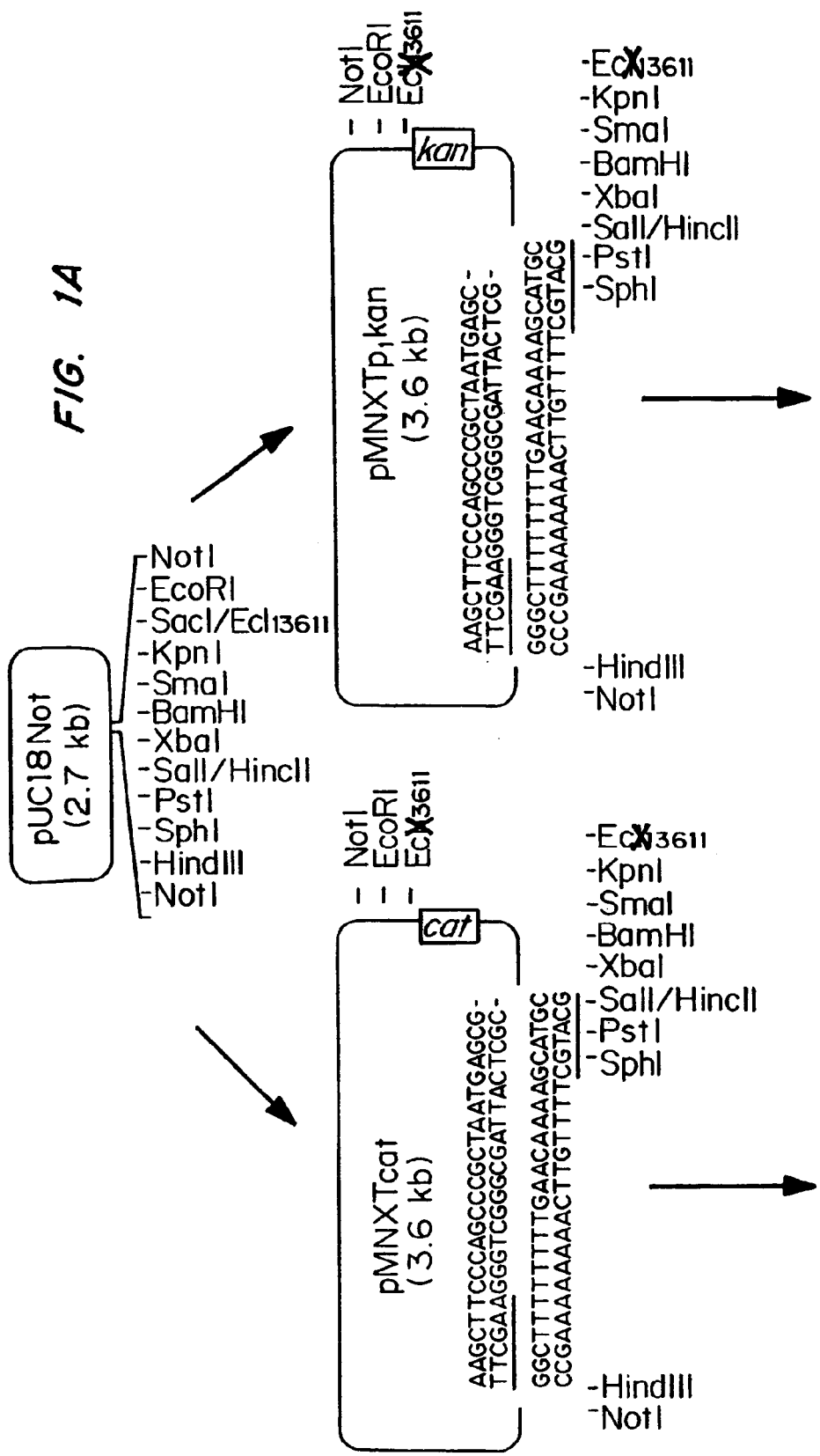
FIGS. 1A–1C are a diagram showing the construction of pMNXTp$_1$kan, pMNXTp$_1$cat, pMSXTp$_1$kan, and pMSXTp$_1$cat. The inserted sequences are SEQ ID NO: 1 and SEQ ID NO: 2.

By randomly inserting genes that encode PHA biosynthetic enzymes into the chromosome of *E. coli*, means have been identified to directly achieve high levels of expression from strong endogenous promoters at sites that are non-essential for growth of the host in industrial medium based fermentations. As demonstratd by the examples, *E. coli* strains have been obtained using these techniques that produce PHAs in levels exceeding 85% of the cell dry weight from single copy genes on the chromosome. Expression of the phb genes in these strains is not dependent on the upstream sequences of phbC in *R. eutropha* nor on a high copy number construct. Maintenance of the phb genes by these strains is independent of the supplementation of antibiotics, the presence of stabilizing loci such as parB or hok/sok or any other selective pressure. The ultra-high level of expression required in the plasmid-based systems has been found to be completely unnecessary. Furthermore, unlike the most successful fermentations reported to date (Wang & Lee, *Biotechnol. Bioeng.* 58:325–28 (1998)) for recombinant plasmid-based *E. coli*, fermentation with these strains provides that virtually all of the cells contain PHB at the end of the fermentation.

Despite the low copy number, these transgenic bacteria accumulate PHB to levels observed for wild-type organisms. The host used for recombinant PHB production also is an important parameter in designing a plasmid-based *E. coli* system. For example, although W3110 strains were poor PHB producers when using a plasmid-based system, it was found that by integrating the phb genes into the chromosome of this same host, the host retained excellent growth characteristics while accumulating commercially significant levels of PHB.

Methods and Materials for Producing the Microbial Strains
Bacterial Strains to be Modified A number of bacteria can be genetically engineered to produce polyhydroxyalkanoates. These include organisms that already produce polyhydroxyalkanoates, modified to utilize alternative substrates or incorporate additional monomers, or to increase production, and organisms that do not produce polyhydroxyalkanoates, but which expresses none to some of the enzymes required for production of polyhydroxylkanoates. Examples include *E. coli, Alcaligenes latus, Alcaligenese eutrophus, Azotobacter, Pseudomonas putida*, and *Ralstonia eutropha*.

Methods for Generating Transgenic PHB Producers

Methods for incorporating engineered gene constructs into the chromosomal DNA of bacterial cells are well known to those skilled in the art. Typical integration mechanisms include homologous recombination using linearized DNA in recBC or recD strains followed by P1 transduction (Miller 1992, A Short Course in Bacterial Genetics: A laboratory manual & Handbook for *Escherichia coli* and Related Bacteria. Cold Spring Harbor laboratory Press, Cold Spring Harbor, N.Y.) special plasmids (Hamilton et al.,*J. Bacteriol.* 171:4617 (1989); Metcalf et al., *Plasmid* 35:1 (1996); U.S. Pat. No. 5,470,727 to Mascarenhas et al.), or by random insertion using transposon based systems (Herrero et al. *J. Bacteriol.* 172:6557 (1990); Peredelchuk & Bennett, *Gene* 187:231 (1997); U.S. Pat. No. 5,595,889 to Richaud et al.; U.S. Pat. No. 5,102,797 to Tucker et al.). In general, the microbial strains containing an insertion are selected on the basis of an acquired antibiotic resistance gene that is supplied by the integrated construct. However, complementation of auxotrophic mutants can also be used.

Expression of the genes of interest for chromosomal integration can be achieved by including a transcription activating sequence (promoter) in the DNA construct to be integrated. Site-directed, homologous recombination can be combined with amplification of expression of the genes of interest, as described by U.S. Pat. No. 5,00,000 to Ingram et al. Although mini-transposon systems have been used for a number of years, they have been designed such that the expression level of the integrated gene of interest is not modulated. Ingram, et al. selected for increased expression of a foreign gene inserted into the *E. coli* chromosome by homologous recombination. This was achieved by inserting a promoter-less chloroamphenicol (Cm) resistance gene downstream of the gene of interest to create a transcriptional fusion. After a transcriptional fusion of the alcohol dehydrogenase gene with a promoterless chloramphenicol acetyl transferase genes is integrated in the pfl gene, increased expression is achieved by selecting mutants on increasing concentrations of chloramphenicol. However, in chemostat studies these stabilzed strains still lost the capacity to produce ethanol (Lawford & Rousseau, *Appl. Biochem. Biotechnol.* 57–58:293–305 (1996)). Also, strains that contained the ethanologenic genes on the chromosome demonstrated a decreased growth rate in glucose minimal medium (Lawford & Rousseau, *Appl. Biochem. Biotechnol.*, 57–58:277–92 (1996)).

These approaches have been combined and modified to randomly integrate a mini-transposon into the chromosome to select for healthy, fast growing transgenic strains coupled with a screening system for modulating expression of the integrated genes. A series of expression cassettes have been developed for inserting heterologous genes into bacterial chromosomes. These cassettes are based on the transposon delivery systems described by Herrero et al., *J. Bacteriol.* 172:6557–67 (1990); de Lorenzo et al., *J. Bacteriol.* 172:6568 (1990). Although these systems specify RP4-mediated conjugal transfer and use only transposon Tn10 and Tn5, any combination of transposon ends and delivery system could be adapted for the technology described, resulting in sustained and homogeneous PHA production.

The following general approach is used for generating transgenic *E. coli* PHB producers: (1) a promoterless antibiotic resistance (abr) gene is cloned in the polylinker of a suitable plasmid such as pUC18NotI or pUC18SfiI so that the major part of the polylinker is upstream of abr; (2) phb genes are subsequently cloned upstream of and in the same orientation as the abr gene; (3) the phb-abr cassette is excised as a NotI or AvrII fragment (AvrII recognizes the SfiI site in pUC18SfiI) and cloned in the corresponding sites of any plasmid like those from the pUT- or pLOF-series; (4) the resulting plasmids are maintained in *E. coli* λpir strains and electroporated or conjugated into the *E. coli* strain of choice in which these plasmids do not replicate; and (5) new strains in which the phb-abr cassette has successfully integrated in the chromosome are selected on selective medium for the host (e.g., naladixic acid when the host is naladixic acid resistant) and for the cassette (e.g., chloramphenicol, kanamycin, tetracyclin, mercury chloride, bialaphos). The resulting phb integrants are screened on minimal medium in the presence of glucose for growth and PHB formation.

Several modifications of this procedure can be made. If the promotorless antibiotic resistance marker is not used, the insertion of the PHA genes is selected based on a marker present in the vector and integrated strains producing the desired level of PHA are detected by screening for PHA production. The phb genes may have, but do not need, endogeneous transcription sequences, such as upstream activating sequences, RNA polymerase binding site, and/or operator sequences. If the phb genes do not have such sequences, the described approach is limited to the use of vectors like the pUT series in which transcription can proceed through the insertion sequences. This limitation is due to the inability of RNA polymerase to read through the Tn10 flanking regions of the pLOF plasmids. The abr gene may carry its own expression sequences if so desired. Instead of an abr gene, the construct may be designed such that an essential gene serves as selective marker when the host strain has a mutation in the corresponding wild-type gene. Examples of genes useful for this purpose are generally known in the art. Different constructs can be integrated into one host, either subsequently or simultaneously, as long as both constructs carry different marker genes. Using multiple integration events, phb genes can be integrated separately, e.g., the PHB polymerase gene is integrated first as a phbC-cat cassette, followed by integration of the thiolase and reductase genes as a phbAB-kan cassette. Alternatively, one cassette may contain all phb genes whereas another cassette contains only some phb genes required to produce a desired PHA polymer.

In some cases a transposon integration vector such as pJMS11 (Panke et al. *Appl. Enviro. Microbiol.* 64: 748–751) may be used such that the selectable marker can be excised from the chromosome of the integrated strain. This is useful for a number of reasons including providing a mechanism to insert multiple transposon constructs using the same marker gene by excising the marker following each insertion event.

Sources of phb and Other Genes Involved in PHA Formation

A general reference is Madison and Huisman, 1999, *Microbiology and Molecular Biology Reviews* 63: 21–53. The phb genes may be derived from different sources and combined in a single organism, or from the same source.

Thiolase Encoding Genes

Thiolase encoding genes have been isolated from *Alcaligenes latus, Ralstonia eutropha* (Peoples & Sinskey, *J. Biol. Chem.* 264(26):15298–303 (1989); *Acinetobacter* sp. (Schembri, et al., *J. Bacteriol.* 177(15):4501–7 (1995)), *Chromotium vinosum* (Liebergesell & Steinbuchel, *Eur. J. Biochem.* 209(1,:135–50 (1992)), *Pseudomonas acidophila, Pseudomonas denitrificans* (Yabutani, et al., *FEMS Microbiol. Lett.* 133 (1–2):85–90 (1995)), *Rhizobium meliloti* (Tombolini, et al., *Microbiology* 141:2553–59 (1995)), *Thiocystis violacea* (Liebergesell & Steinbuchel, *Appl. Microbiol. Biotechnol.* 38(4):493–501 (1993)), and *Zoogloea ramigera* (Peoples, et al., *J. Biol. Chem.* 262(1):97–102 (1987)).

Other genes that have not been implicated in PHA formation but which share significant homology with the phb genes and/or the corresponding gene products may be used as well. Genes encoding thiolase- and reductase-like enzymes have been identified in a broad range of non-PHB producing bacteria. *E. coli* (U29581, D90851, D90777), *Haemophilus influenzae* (U32761), *Pseudomonas fragi* (D10390), *Pseudomonas aeruginosa* (U88653), *Clostridium acetobutylicum* (U08465), *Mycobacterium leprae* (U00014), *Mycobacterium tuberculosis* (Z73902), *Helicobacter pylori* (AE000582), *Thermoanaerobacterium thermosaccharolyticum* (Z92974), *Archaeoglobus fulgidus* (AE001021), *Fusobacterium nucleatum* (U37723), *Acinetobacter calcoaceticus* (L05770), *Bacillus subtilis* (D84432, Z99120, U29084), and *Synechocystis* sp. (D90910) all encode one or more thiolases from their chromosome. Eukaryotic organisms such as *Saccharomyces cerevisiae* (L20428), *Schizosaccharomyces pombe* (D89184), *Candida tropicalis* (D13470), *Caenorhabditis elegans* (U41105), human (S70154), rat (D13921), mouse (M35797), radish (X78116), pumpkin (D70895), and cucumber (X67696) also express proteins with significant homology to the 3-ketothiolase from *R. eutropha*.

Reductase Encoding Genes

Reductase encoding genes have been isolated from *A. latus, R. eutropha* (Peoples & Sinskey, *J. Biol. Chem.* 264(26):15298–303 (1989); *Acinetobacter* sp. (Schembri, et al., *J. Bacteriol.* 177(15):4501–7 (1995)), *C. vinosum* (Liebergesell & Steinbuchel, *Eur. J. Biochem.* 209(1): 135–50 (1992)), *P. acidophila, P. denitrificans* (Yabutani, et al., *FEMS Microbiol. Lett.* 133 (1–2):85–90 (1995)), *R. meliloti* (Tombolini, et al., *Microbiology* 141:2553–59 (1995)), and *Z. ramigera* (Peoples, et al., *J. Biol. Chem.* 262(1):97–102 (1987)).

Other genes that have not been implicated in PHA formation but which share significant homology with the phb genes and/or the corresponding gene products may be used as well. Genes with significant homology to the phbB gene encoding acetoacetyl CoA reductase have been isolated from several organisms, including *Azospirillum brasiliense*

(X64772, X52913) *Rhizobium* sp. (U53327, Y00604), *E. coli* (D90745), *Vibrio harveyi* (U39441), *H. influenzae* (U32701), *B. subtilis* (U59433), *P. aeruginosa* (U91631), *Synechocystis* sp. (D90907), *H. pylori* (AE000570), *Arabidopsis thaliana* (X64464), *Cuphea lanceolata* (X64566) and *Mycobacterium smegmatis* (U66800).

PHA Polymerase Encoding Genes

PHA polymerase encoding genes have been isolated from *Aeromonas caviae* (Fukui & Doi, *J. Bacteriol.* 179(15): 4821–30 (1997)), *A. latus, R. eutropha* (Peoples & Sinskey, *J. Biol. Chem.* 264(26):15298–303 (1989); *Acinetobacter* (Schembri, et al., *J. Bacteriol.* 177(15):4501–7 (1995)), *C. vinosum* (Liebergesell & Steinbuchel, *Eur. J. Biochem.* 209(1):135–50 (1992)), *Methylobacterium extorquens* (Valentin & Steinbuchel, *Appl. Microbiol. Biotechnol.* 39(3): 309–17 (1993)), *Nocardia corallina* (GenBank Acc. No. AF019964), *Nocardia salmonicolor, P. acidophila, P. denitrificans* (Ueda, et al., *J. Bacteriol.* 178(3):774–79 (1996)), *Pseudomonas aeruginosa* (Timm & Steinbuchel, *Eur. J. Biochem.* 209(1):15–30 (1992)), *Pseudomonas oleovorans* (Huisman, et al., *J. Biol. Chem.* 266:2191–98 (1991)), *Rhizobium etli* (Cevallos, et al., *J. Bacteriol.* 178(6): 1646–54 (1996)), *R. meliloti* (Tombolini, et al., *Microbiology* 141 (Pt 10):2553–59 (1995)), *Rhodococcus ruber* (Pieper & Steinbuchel, *FEMS Microbiol. Lett.* 96(1):73–80 (1992)), *Rhodospirrilum rubrum* (Hustede, et al., *FEMS Microbiol. Lett.* 93:285–90 (1992)), *Rhodobacter sphaeroides* (Steinbuchel, et al., *FEMS Microbiol. Rev.* 9(2–4): 217–30 (1992); Hustede, et al., *Biotechnol. Lett.* 15:709–14 (1993)), *Synechocystis* sp. (Kaneko, *DNA Res.* 3(3):109–36 (1996)), *T. violaceae* (Liebergesell & Steinbuchel, *Appl. Microbiol. Biotechnol.* 38(4: 493–501 (1993)), and *Z. ramigera* (GenBank Acc. No. U66242).

Vectors for Incorporation of Genes into the Bacterial Chromosomes

The pUT and pLOF series of plasmid transposon delivery vectors useful in the PHA-producing methods described herein use the characteristics of transposon Tn5 and transposon Tn10, respectively. The transposase genes encoding the enzymes that facilitate transposition are positioned outside of the transposase recognition sequences' and are consequently lost upon transposition. Both Tn5 and Tn10 are known to integrate randomly in the target genome, unlike, for example, the Tn7 transposon. However, generally any transposon can be modified to facilitate the insertion of heterologous genes, such as the phb genes, into bacterial genomes. This methodology thus is not restricted to the vectors used in the methods described herein.

Methods and Materials for Screening for Enhanced Polymer Production

Screening of Bacterial Strains

The technology described above allows for the generation of new PHA producing strains and also provides new bacterial strains that are useful for screening purposes. Table 1 below shows the different combinations of chromosomally and plasmid encoded PHB enzymes and how specific strains can be used to identify new or improved enzymes.

Besides a screening tool for genes that express improved enzymes, *E. coli* strains with a complete PHA pathway integrated on the chromosome can be used to screen for heterologous genes that affect PHA formation. *E. coli* is a useful host because genes are easily expressed from a multitude of plasmid vectors: high copy-number, low copy-number, chemical or heat inducible, etc. and mutagenesis procedures have been well established for this bacterium. In addition, the completely determined genomic sequence of *E. coli* facilitates the characterization of genes that affect PHA metabolism.

Transgenic *E. coli* strains expressing an incomplete PHA pathway can be transformed with gene libraries to identify homologs of the missing gene from other organisms, either prokaryotic or eukaryotic. Because these screening strains do not have the complete PHA biosynthetic pathway, the missing functions can be complemented and identified by the ability of the host strain to synthesize PHA. Generally PHA synthesizing bacterial colonies are opaque on agar plates, whereas colonies that do not synthesize PHA appear translucent. Clones from a gene library that complement the missing gene confer a white phenotype to the host when grown on screening media. Generally screening media contains all essential nutrients with excess carbon source and an antibiotic for which resistance is specified by the vector used in the library construction.

Besides new genes, genes encoding improved PHA biosynthetic enzymes can also be screened for. A mutagenized collection of plasmids containing a phb biosynthetic gene into an *E. coli* host strain lacking this activity but containing genes encoding the other PHA biosynthetic enzymes can be screened for increased or altered activity. For example, PHA polymerases with increased activity can be screened for in a strain that expresses thiolase and reductase from the chromosome by identifying PHB-containing colonies under conditions that support PHB formation poorly. mcl-PHA polymerases with an increased specificity towards $C_4$ can similarly be screened for under PHB accumulation promoting conditions. Altered activities in the phaG encoded ACP::CoA transferase can be screened for by expressing mutated versions of this gene in a phbC integrant and screening for PHB formation from short chain fatty acids. Enzymes that have increased activity under sub-optimal physical conditions (e.g., temperature, pH, osmolarity, and oxygen tension) can be screened for by growing the host under such conditions and supplying a collection of mutated versions of the desired gene on a plasmid. Reductase enzymes with specificity to medium side-chain 3-ketoacyl-CoA's, such as 3-ketohexanoyl-CoA, can be screened for by identifying PHA synthesizing colonies in a strain that has a msc-PHA polymerase gene integrated on the chromosome and mutagenized versions of a phbB gene on a plasmid. The combination of different specificity PHA enzymes allows for the screening of a multitude of new substrate specificities. Further permutations of growth conditions allows for screening of enzymes active under sub-optimal conditions or enzymes that are less inhibited by cellular cofactors, such as Coenzyme A and CoA-derivatives, reduced or oxidised nicotinamide adenine dinucleotide or nicotinamide adenine dinucleotide phosphate (NAD, NADP, NADH, and NADPH).

Using the techniques described herein, *E. coli* strains expressing the genes encoding enzymes for the medium side-chain PHA pathway can be constructed. Strains in which either phaC or phaG or both are integrated on the chromosome of *E. coli* accumulate a PHA including medium chain-length 3-hydroxy fatty acids of which 3-hydroxydecanoate is the predominant constituent. When phaC is integrated by itself, msc-PHAs can be synthesized from fatty acids. In such strains, it is advantageous to manipulate fatty acid oxidation such that 3-hydroxy fatty acid precursors accumulate intracellularly. This manipulation can be achieved by mutagenesis or by substituting the *E. coli* fatty acid degradation enzymes FadA and FadB encoding genes with the corresponding faoAB genes from *Pseudomonas putida* or related rRNA homogy group I fluorescent pseudomonad.

TABLE 1

Phenotypes of Strains for Screening of New or Improved Enzymes

| Genes integrated on chromosome | Gene(s) on plasmid | Carbon source for screen | Screen identifies genes encoding |
|---|---|---|---|
| phbC | library | glucose | new thiolase/reductase |
|  | library | fatty acids | new reductase, hydratase, transferase |
|  | library | hydroxy fatty acid, e.g. 4-hydroxybutyrate (4HB) | hydroxy fatty acid activating enzyme, e.g. 4HB-CoA transferase (acetyl-CoA or succinyl-CoA dependent) or 4HB-CoA synthase |
|  | phaG | glucose | transferase with new substrate specificity |
| phbAB | library | glucose | new polymerase gene |
|  | phaC | glucose; altered environmental conditions | polymerase with new substrate specificity; increased activity under sub-optimal conditions |
| phbBC | library | glucose | new thiolase |
|  | phbA | limiting glucose/less prefered carbon sources or rich medium; altered environmental conditions | deregulated thiolase; increased activity under sub-optimal conditions |
| phbAC | library | glucose | new reductase |
|  | phbB | limiting glucose/less prefered carbon sources or rich medium; altered environmental conditions | deregulated reductase; increased activity under sub-optimal conditions |
| phbCAB | library | any | enzymes affecting PHB formation under specific conditions |
| phbCAB, random mutations (chemical or transposon) |  | any | enzymes affecting PHB formation under specific conditions |
| phaC | library | hexanoate | hydratase with specificity for C6 and longer substrates |
|  | phaJ | fatty acids | hydratase with increased specificity for C6 and longer substrates |
|  | phbB | fatty acids | reductase with new substrate specificity |
| phaC fadR+, Δato | phbAB | glucose + butyrate | thiolase/reductase combination specific for C6 monomer |
| phaJ | phaC | fatty acids | polymerase with wider substrate specificity |
| phaG | phbC | glucose | polymerase with wider substrate specificity |

EXAMPLES

The methods and compositions described herein will be further understood by reference to the following non-limiting examples. These examples use the following general methods and materials.

Materials and Methods

E. coli strains were grown in Luria-Bertani medium (Sambrook, et al., *Molecular Cloning: A Laboratory Manual,* 2d ed. (Cold Spring Harbor Laboratory Press, Cold Spring Harbor, N.Y. [1992 at 37° C. or 30° C. or in minimal E2 medium (Lageveen et al., *Appl. Environ. Microbiol* 54: 2924–2932 (1988)). DNA manipulations were performed on plasmid and chromosomal DNA purified with the Qiagen plasmid preparation or Qiagen chromosomal DNA preparation kits according to manufacturers recommendations. DNA was digested using restriction enzymes (New England Biolabs, Beverly, Mass.) according to manufacturers recommendations. DNA fragments were isolated from 0.7% agarose-Tris/acetate/EDTA gels using a Qiagen kit.

Plasmid DNA was introduced into E. coli cells by transformation or electroporation (Sambrook, et al., *Molecular Cloning: A Laboratory Manual,* 2d ed. (Cold Spring Harbor Laboratory Press, Cold Spring Harbor, N.Y.)). Transposition of phb genes from the pUT vectors was achieved by mating of the plasmid donor strain and the recipient (Herrero et al., *J. Bacteriol.* 172:6557 (1990)). The recipient strains used were spontaneous naladixic acid or rifampicin resistant mutants of E. coli derived from either LS5218 or MBX23. MBX23 is LJ14 rpoS::Tn10 in which the rpoS::Tn10 allele was introduced by P1 transduction from strain 1106 (Eisenstark). Recipients in which phb genes have been integrated into the chromosome were selected on naladixic acid or rifampicin plates supplemented with the antibiotic resistance specified by the mini-transposon, kanamycin, or chloramphenicol. Oligonucleotides were purchased from Biosynthesis or Genesys. DNA sequences were determined by automated sequencing using a Perkin-Elmer ABI 373A sequencing machine. DNA was amplified using the polymerase-chain-reaction in 50 microliter volume using PCR-mix from Gibco-BRL (Gaithersburg, Md.) and an Ericomp DNA amplifying machine.

DNA fragments were separated on 0.7% agarose/TAE gels. Southern blots were performed according to procedures described by Sambrook, et al., *Molecular Cloning: A Laboratory Manual,* 2d ed. (Cold Spring Harbor Laboratory Press, Cold Spring Harbor, N.Y.). Detection of DNA fragments containing phb genes was performed using chemiluminescent labeling and detection kits from USB/Amersham. Proteins samples were denatured by incubation in a boiling water bath for 3 minutes in the presence of 2-mercaptoethanol and sodium dodecylsulphate and subsequently separated on 10%, 15%, or 10–20% sodium dodecylsulphate-polyacrylamide gels. After transfer of protein to supported nitrocellulose membranes (Gibco-BRL, Gaithersburg, Md.), 3-ketoacyl-CoA thiolase, acetoacetyl-CoA reductase and PHB polymerase was detected using polyclonal antibodies raised against these enzymes and horseradish peroxidase labeled secondary antibodies followed by chemiluminescent detection (USB/Amersham).

Acetoacetyl-CoA thiolase and acetoacetyl-CoA reductase activities were determined as described by Peoples and Sinskey, J. Biol. Chem. 264: 15293–15297 (1989) in cell free extracts from strains grown for 16 hours in LB-medium at 37 C. The acetoacetyl-CoA thiolase activity is measured as degradation of a $Mg^{2+}$-acetoacetyl-CoA complex by monitoring the decrease in absorbance at 304 nm after addition of cell-free extract using a Hewlett-Packer spectrophotometer. The acetoacetyl-CoA reductase activity is measured by monitoring the conversion of NADH to NAD at 340 nm using a Hewlett-Packer spectrophotometer.

Accumulated PHA was determined by gas chromatographic (GC) analysis as follows. About 20 mg of lyophilized cell mass was subjected to simultaneous extraction and butanolysis at 110 C. for 3 hours in 2 mL of a mixture containing, by volume, 90% 1-butanol and 10% concentrated hydrochloric acid, with 2 mg/mL benzoic acid added as an internal standard. The water-soluble components of the resulting mixture were removed by extraction with 3 mL water. The organic phase (1 µL at a split ratio of 1:50 at an overall flow rate of 2 mL/min) was analyzed on an HP 5890 GC with FID detector (Hewlett-Packard Co, Palo Alto, Calif.) using an SPB-1 fused silica capillary GC column (30 m; 0.32 mm ID; 0.25 µm film; Supelco; Bellefonte, Pa.) with the following temperature profile: 80° C., 2 min.; 10° C. per min. to 250° C.; 250° C., 2 min. The standard used to test for the presence of 4-hydroxybutyrate units in the polymer was γ-butyrolactone, which, like poly(4-hydroxybutyrate), forms n-butyl 4-hydroxybutyrate upon butanolysis. The standard used to test for 3-hydroxybutyrate units in the polymer was purified PHB.

The molecular weights of the polymers were determined following chloroform extraction by gel permeation chromatography (GPC) using a Waters Styragel HT6E column (Millipore Corp., Waters Chromatography Division, Milford, Mass.) calibrated versus polystyrene samples of narrow polydispersity. Samples were dissolved in chloroform at 1 mg/mL, and 50 µL samples were injected and eluted at 1 mL/min. Detection was performed using a differential refractometer.

1-Methyl-3-nitro-1-nitroso-guanidine (NTG) mutagenesis was performed as described by Miller, *A Short Course in Bacterial Genetics* (Cold Spring Harbor Laboratory Press, Cold Spring Harbor, N.Y.) using a 90 minute treatment with 1 mg/ml NTG corresponding to 99% killing.

Example 1

Host Strains and Plasmid Tools for Gene Integration

Strains and plasmids from which transposon vectors and transposon derivatives were developed are listed in Tables 2 and 3 below. MBX245 and MBX247 were selected by growing MBX23 and LS5218 respectively on LB plates containing approximately 30 g/ml naladixic acid. MBX246 and MBX248 were selected by growing MBX23 and LS5218, respectively, on LB plates containing 50 g/ml rifampicin. Colonies that appeared on these selective media within 24 hours were replica plated on the same medium and after growth stored in 15% glycerol/nutrient broth at −80° C.

MBX245 and MBX247 were selected by growing MBX23 and LS5218 respectively on LB plates containing 30 µg/ml naladixic acid. MBX246 and MBX248 were selected by growing MBX23 and LS5218 respectively on LB plates containing 50 µg/ml rifampicin. Colonies that appeared on these selective media within 24 hours were replica plated on the same medium and after growth stored in 15% glycerol/nutrient broth at −80° C.

TABLE 2

Host Strains Used For Gene Integration

| strain | genotype | source |
| --- | --- | --- |
| DH5α | recA1 endA1 gyrA96 thi hsdR17 supE44 relA1 Δ(lac-proAB) (Φ80dlacΔ(lacZ)M15) | 1 |
| S17-1 λpir | recA thi pro hsdR⁻M⁺ RP4:2-Tc::Mu::Km Tn7 λpir lysogen | 2 |
| CC118 λpir | Δ(ara-leu) araD ΔlacX74 galE galK phoA20 thi-1 rpsE rpoB argE(Am) recA1, λpir lysogen | 2 |
| XL1-Blue | F'::Tn10 lacI^q Δ(lacZ) M15 proAB/recA1 endA1 gyrA96 thi hsdR17 supE44 relA1 Δ(lac-proAB) | 3 |
| LS5218 | fadR601 atoC512^c | Spratt et al, 1981 J. Bacteriol. 146: 1166–1169 |
| LJ14 | LS5218 atoC2^c atoA14 | Spratt et al, 1981 J. Bacteriol. 146: 1166–1169 |
| MBX23 | LJ14 rpoS | Metabolix, Inc. |
| MBX245 | MBX23 Nl^r | Metabolix, Inc. |
| MBX246 | MBX23 Rf^r | Metabolix, Inc. |
| MBX247 | LS5218 Nl^r | Metabolix, Inc. |
| MBX248 | LS5218 Rf^r | Metabolix, Inc. |

1. New England Biolabs (Beverly, MA)
2. Herrero et al., J. Bacteriol. 172:6557–67 (1990)
3. Stratagene (San Diego, CA)

TABLE 3

Plasmids Used For Gene Integration

| plasmid | characteristics | source |
| --- | --- | --- |
| pUC18Not | Ap^r, NotI sites flanking polylinker | 2 |
| pUC18Sfi | Ap^r, SfiI sites flanking polylinker | 2 |
| pUTkan | Ap^r, Km^r, oriR6K, mobRP4 depends on λpir for replication | 2 |
| pUTHg | Ap^r, Hg^r, oriR6K, mobRP4 depends on λpir for replication | 2 |
| pKPS4 | Ap^r, phaC1 from *Pseudomonas oleovorans* | |
| pUCDBK1 | Ap^r, phbA and phbB from *Zoogloea ramigera* | Peoples and Sinskey 1989, Molecular Microbiol.3: 349–357 |
| pZS | Ap^r, phbC from *Zoogloea ramigera* | WO 99/14313 |

Example 2

Construction of Cloning Vectors to Facilitate Integration of phb Genes

Figure 1B:
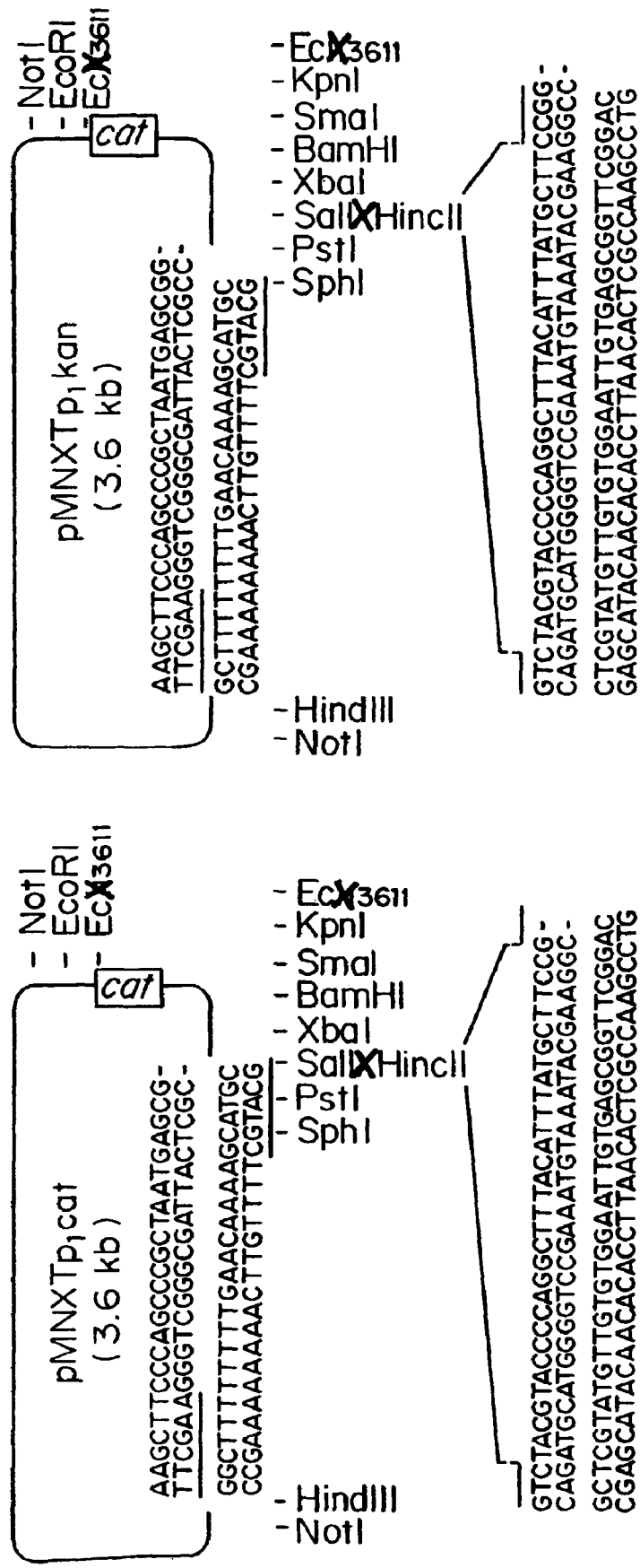
Figure 1C:
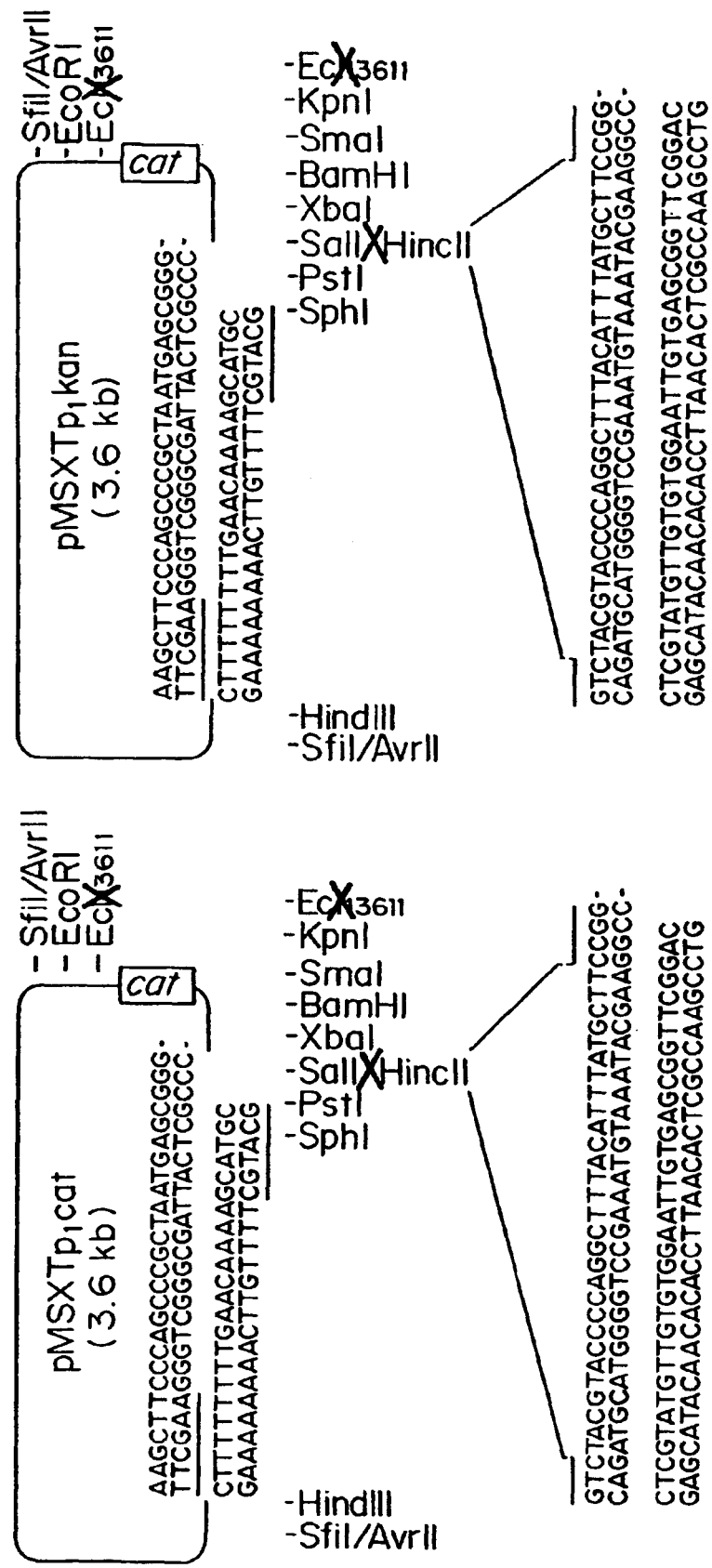

The plasmids pMNXTp1kan and pMNXTp1 cat were based on the plasmids pUC18Not and pUC18Sfi and developed as shown in FIGS. 1A–1C.

The Tn903 kanamycin (Km) resistance gene from plasmid pBGS18 was amplifed by PCR using the oligonucleotide primers linkK1,
5'TGCATGCGATATCAATTGTCCA GCCAGAAAGT-GAGG (SEQ ID NO: 15),
and linkK2,
5'ATTTATTCAACAAAGCCGCC (SEQ ID NO: 16).

Prior to PCR amplification, the primers were phosphorylated using T4 polynucleotide kinase using standard procedures. The DNa was amplified using the following program: 1 cycle of 3 min at 95° C., 40 s at 42° C., 2 min at 72° C., followed by 30 cycles of 40 s at 95° C., 40 s at 42° C. and 90 s at 72° C. The DNA then was phenol extracted and treated with T4 DNA polymerase prior to gel purification. The blunt ended 0.8 kb DNA fragment was then inserted into the Ecl136II site in the polylinker of pUC18Not to obtain pMNXkan.

The cat gene was obtained as an HindIII cassette from Pharmacia (Pharmacia Inc. NJ), blunt ended using Klenow fragment of DNA polymerase, and inserted into the Ecl136II site of pUC18Not to obtain pMNXcat.

The trp terminator sequence was constructed by annealing the two synthetic oligonucleotides TERM1 (5'CCCAGCCCGCTAATGAGCGGGCTTTTTTTT GAA-CAA AA 3')(SEQ ID NO: 17) and TERM2 (5'TACGTATTTTGTTCAAAAAAAAGCCCGCTC ATT-AGCGGG CTGGG 3') (SEQ ID NO: 18).

The terminator was then inserted into the HindIII-SphI site of pMNXkan and pMNXcat to obtain pMNXTkan and pMNXTcat, respectively. These vectors were constructed such that any promoter fragment can be added between the SphI and SacI sites. Promoter $p_1$ was constructed by annealing of the synthetic oligonucleotides PHBB1 (5'TACGTACCCCAGGCTTACATTTATGCTTCC GGCTCGTATGTTGT GTGGATTG TGAGCGGTT 3') (SEQ ID NO: 19) and PHBB2 (5'TTCGAACCGCTCACAACCACACAACATACG AGC-CGGAAGC ATAAATGTAAAGCCTGGGG 3')(SEQ ID NO: 20) followed by filling in the ends with Klenow fragment of DNA polyrmerase. The blunt-ended promoter fragment $p_1$ was then inserted into the HincII site of pMNXTkan and pMNXT cat to obtain pMNXTp$_1$kan and pMNXTp$_1$cat, respectively.

Plasmid pMSXTp$_1$cat was constructed by transferring the Tp$_1$cat cassette from pMNXTp$_1$cat as an EcoRI-HindIII fragment into the EcoRI-HindIII site of pUC18Sfi. Similarly, pMSXTp$_1$kan was constructed by transferring the EcoRI-HindIII fragment containing Tp$_1$kan into the EcoRI-HindIII site of pUC18Sfi.

Example 3

Figure 2A:
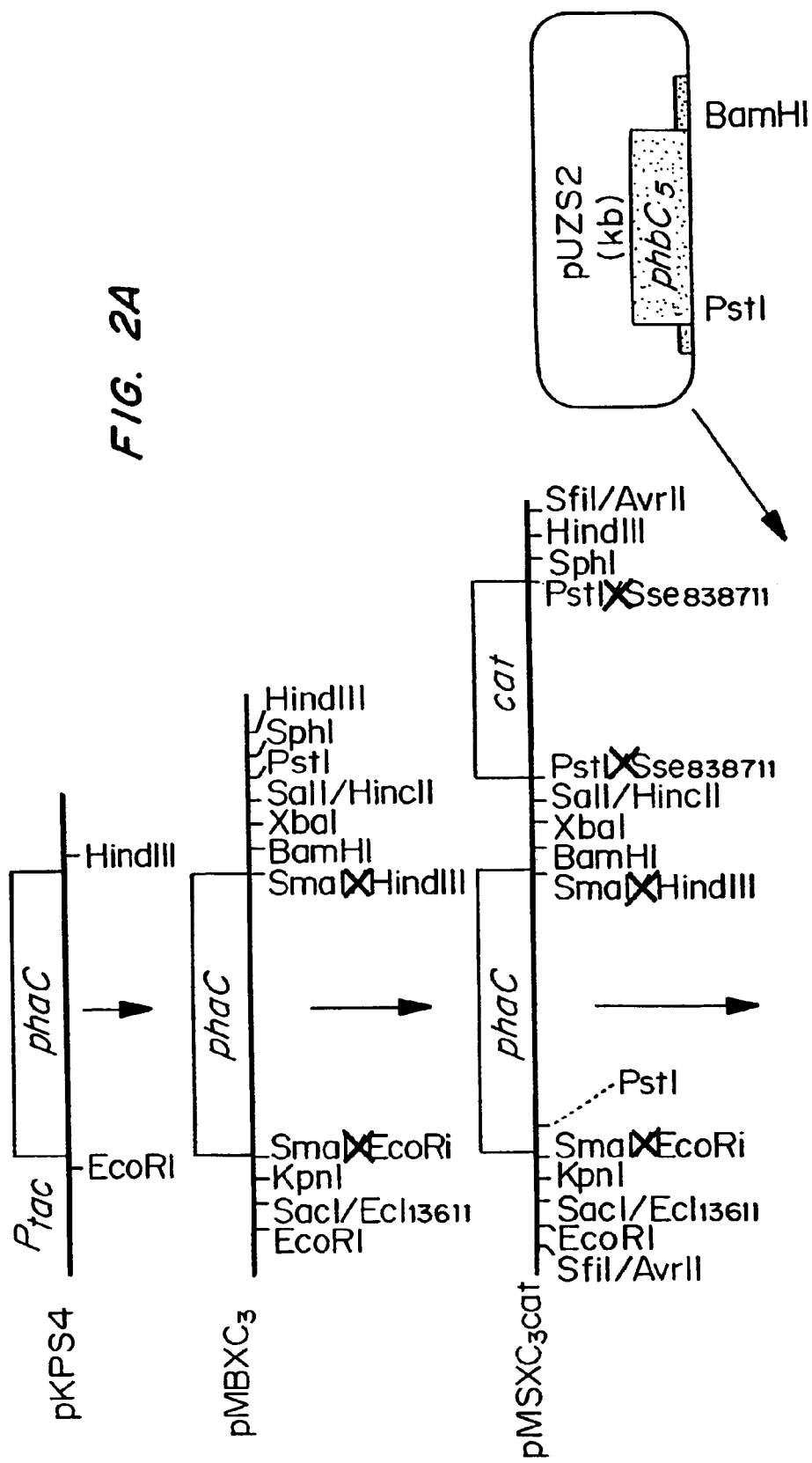
FIGS. 2A and 2B are a diagram showing the construction of pMUXC$_5$cat.
Figure 2B:
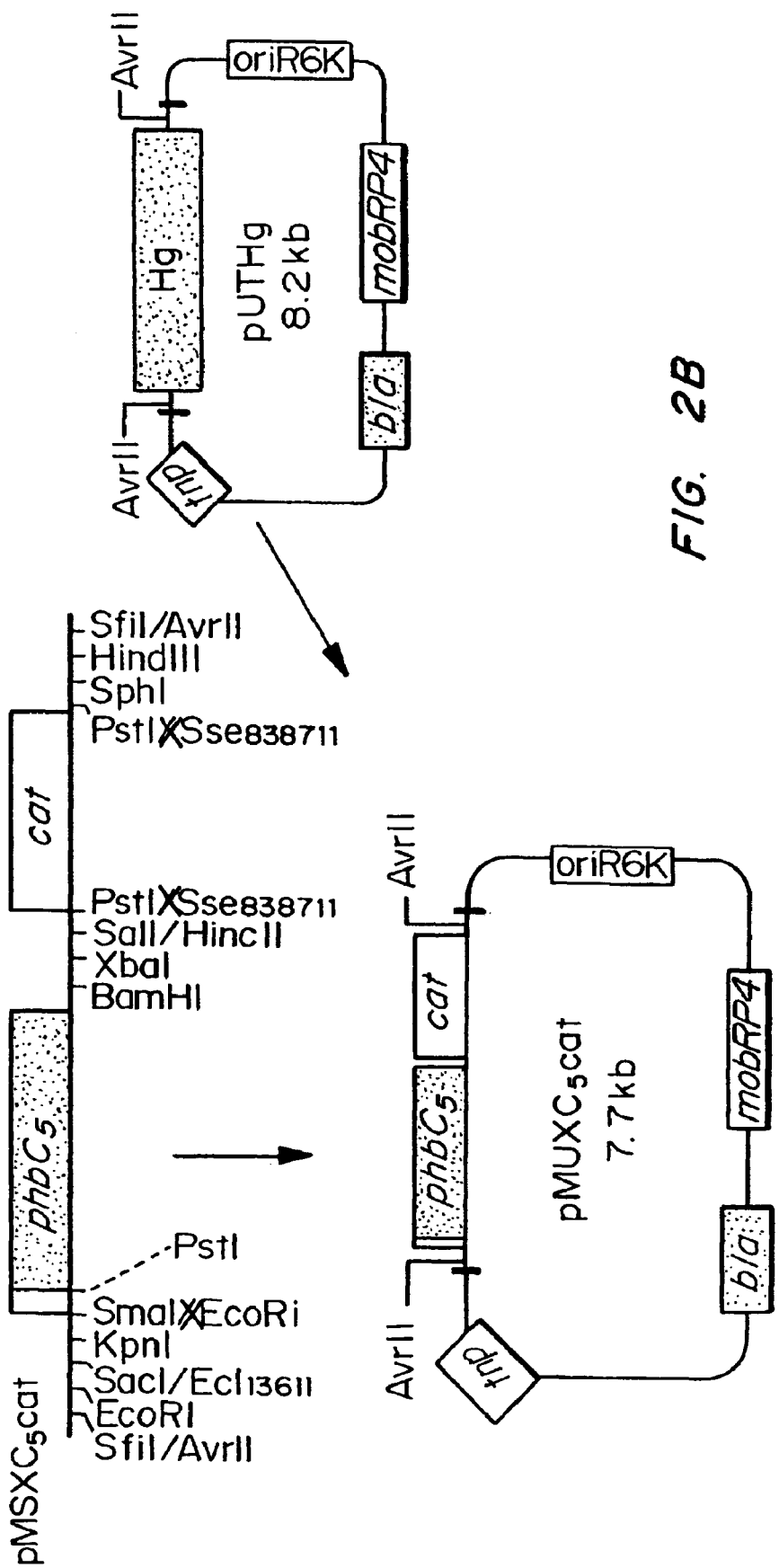

Construction of Plasmids for Chromosomal Integration of phbC, Encoding PHB Polymerase Plasmid pMUXC$_5$cat contains the phbC gene from Z. ramigera on a transposable element for integration of this gene on the chromosome of a recipient strain, as shown in FIGS. 2A and 2B. Strong translational sequences were obtained from pKPS4 which includes phaC1 encoding PHA polymerase from P. oleovorans in the pTrc vector (Pharmacia). In this construct, phaC1 is preceded by a strong ribosome binding site: AGGAGGTTTTT(-ATG) (SEQ ID NO: 21). The phaC1 gene including the upstream sequences, was cloned as a blunt ended EcoRI-HindIII fragment in the SmaI site of pUC18Sfi to give pMSXC$_3$. A blunt ended cat gene cassette was subsequently cloned in the blunt-ended Sse8387 II site, resulting in pMSXC$_3$cat. At this point, all of the phaC1 coding region except the 5' 27 base pairs were removed as a PstI-BamHI fragment and replaced by the corresponding fragment from the phbC gene from Z. ramigera. The resulting plasmid pMSXC$_5$cat encodes a hybrid PHB polymerase enzyme with the 9 amino terminal residues derived from the P. oleovorans PHA polymerase and the remainder from Z. ramigera. The C$_5$cat cassette was then excised as an AvrII fragment and cloned in the corresponding sites of pUTHg, thereby deleting the mercury resistance marker from this vector. The resulting plasmid, pMUXC$_5$cat, contains a C$_5$cat mini-transposon in which phbC is not preceded by a promoter sequence. Expression of the cassette upon integration is therefore dependent on transcriptional sequences that are provided by the DNA adjacent to the integration site.

Example 4

Figure 3A:
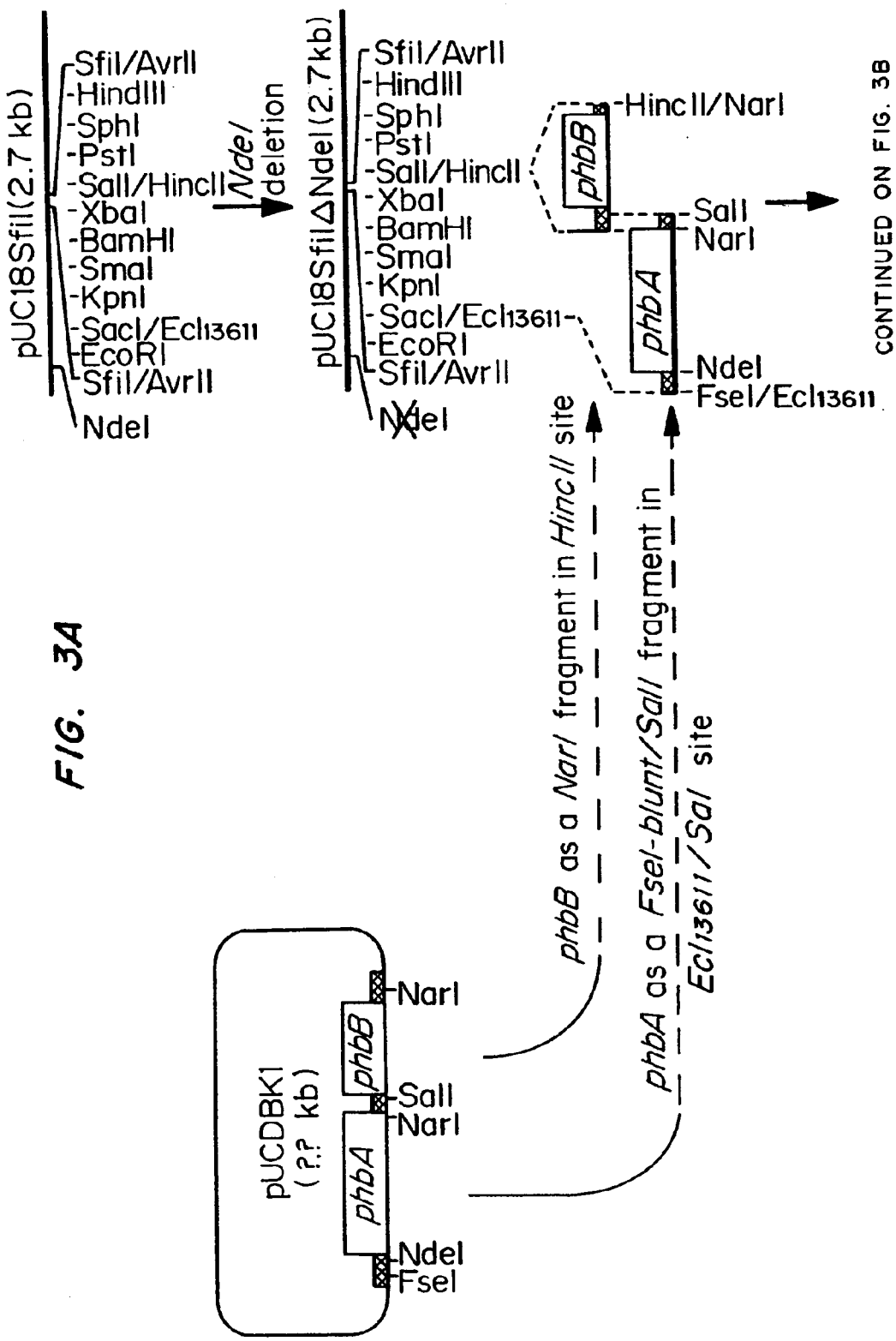
Figure 3B:
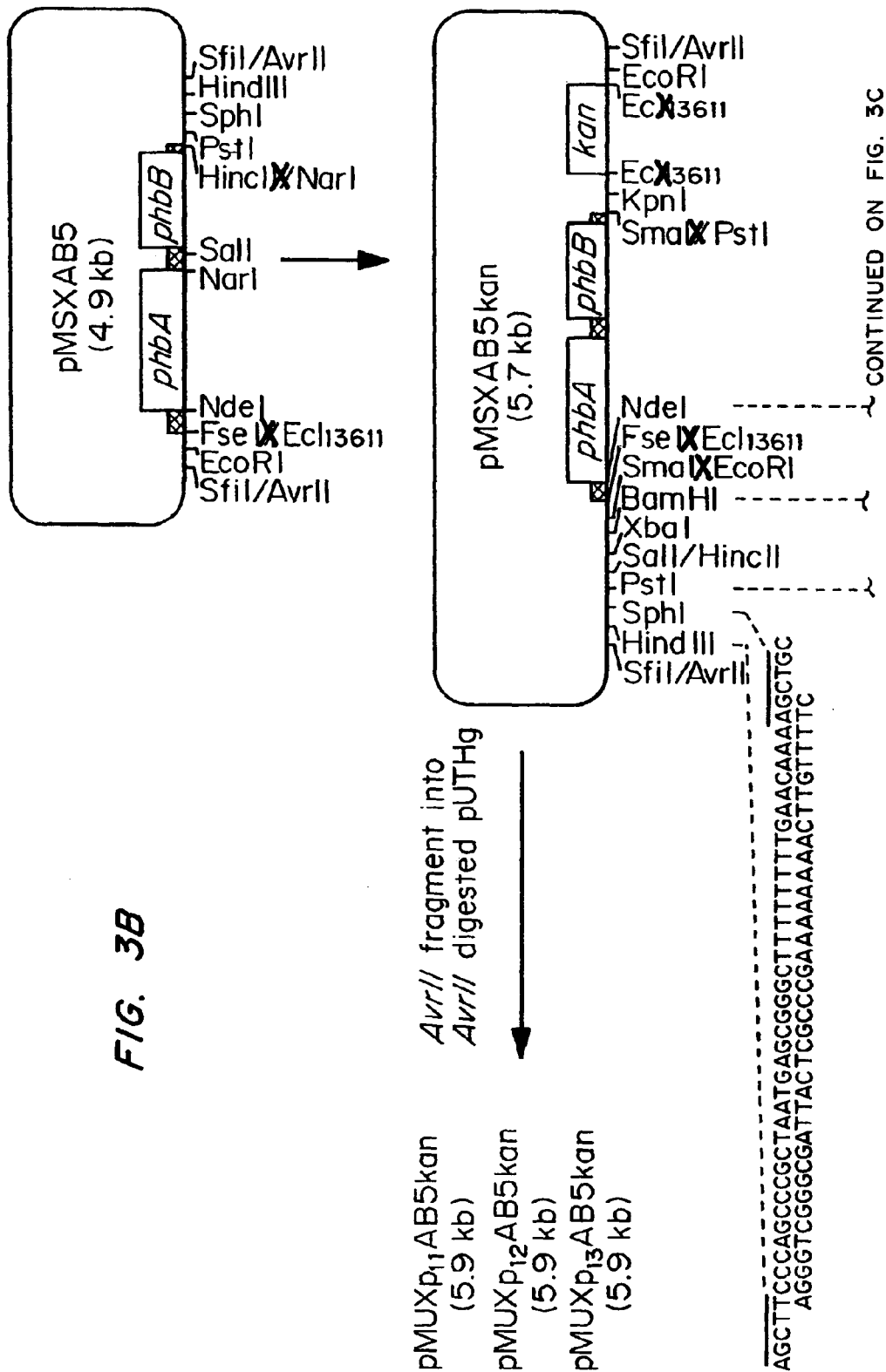

Construction of Plasmids for Chromosomal Integration of phbAB, Encoding Thiolase and Reductase pMSXTp$_1$AB$_5$kan2 was constructed from pMSXTp$_1$kan as partially shown in FIGS. 3A–3C. First pMSXTp$_1$kan was digested with NdeI, filled in with Klenow and religated to obtain pMSXTp$_1$kan2 in which the NdeI site is deleted. This deletion results in a unique NdeI site just upstream of phbA of Z. ramigera during later stages of the cloning procedure.

B$_5$ was cloned as a NarI fragment from pUCDBK1 (Peoples and Sinskey 1989, Molecular Microbiol. 3: 349–357) and cloned in the HincII site of pUC18Sfi to generate pMSXB$_5$. A$_5$ was inserted as an FseI/blunt-SalI fragment in the Ecl136II-SalI sites resulting in pMSXAB$_5$ and regenerating the Z. ramigera AB$_5$ intergenic region. pMSXAB$_5$cat was created by inserting a promoterless cat cassette in the HindIII site of pMSXAB$_5$. The AB$_5$ fragment from pMSXAB$_5$cat was cloned as a EcoRI-PstI fragment into the SmaI site of pMSXTp$_1$kan2 giving pMSXTp$_1$AB$_5$kan2.

The expression cassette AB$_5$cat was then excised as a 2.8 kb AvrII fragment and ligated into the AvrII site of pUTHg and transformed into E. coli strain CC118 λpir to obtain plasmid pMUXAB$_5$cat. This plasmid was then transformed into E. coli S17-1λpir and used to insert the AB5cat expression cassette into the chromosome of E. coli MBX247 by conjugation. The resulting Ap$^s$/Cm$^r$ transconjugants were characterized for integration and expression of the thiolase and reductase genes encoded by the phbAB genes.

Example 5

Construction of Plasmids with Improved Promoters for Integration of phbAB into the Chromosome of E. coli Expression of phbAB5 was improved by introduction of strong promoters upstream of these genes, as shown in FIGS. 3A–3C. These promoters were generated with sets of oligonucleotides that provide upstream activating sequences, a −35 promoter region, a −10 promoter region with transcriptional start site(s), and mRNA sequences with possible stabilizing functions. Plasmid pMSXTp$_1$AB$_5$kan2 was digested with PstI/XbaI, and a fragment containing the −10 region of the lac promoter was inserted as a fragment obtained after annealing oligonucleotides 3A (5'GGCTCGTATAATGTGTGGAGGGAGAACCGC CGGGCTCGCGCCGTT) (SEQ ID NO: 5) and 3B (5'CTAGAACGCGCGAGCCCGGCGGTTCTCCCT CCACACATTATAGAGCCGCA) (SEQ ID NO: 6).

Next, a fragment containing the lac −35 region were inserted into the PstI site as a fragment obtained after annealing the oligonucleotides:

1A
(SEQ ID NO:7)
(5' TTCAGAAAATTATTTTAAATTTCCTCTTGACATTTATGCT GCA)

and 1B
(SEQ ID NO:8)
(5' GCATAAATGTCAAGAGGAAATTTAAAATAATTTTCTGAATGCA).

Next, the messenger stabilizing sequence including the transcriptional start site from AB$_5$ was inserted into the XbaI-NdeI sites as a fragment obtained after annealing the oligonucleotides:

4A
(SEQ ID NO:9)
(5' CTAGTGCCGGACCCGGTTCCAAGGCCGGCCGCAAGGCTGCCAGAAC TGAGGAAGCACA)

-continued and 4B (SEQ ID NO:10)
(5' TATGTGCTTCCTCAGTTCTGGCAGCCTTGCGGCCGGCCTTGGAACC
GGGTCCGGCA).

The resulting plasmid is pMSXp$_{11}$AB$_5$kan2. The AvrII fragment, containing Tp$_{11}$AB$_5$kan2 was cloned into pUTHg cut with AvrII and used for integration into the genome of MBX379 and MBX245.

Plasmid pMSXTp$_{12}$AB$_5$kan2 was constructed as pMSXTP$_{11}$AB$_3$kan2 with the distinction that the following oligonucleotides were used instead of oligonucleotides 1A nd 1B:

2A:

(SEQ ID NO:11)
(5' TCCCCTGTCATAAAGTTGTCACTGCA)

and 2B (SEQ ID NO:12)
(5' GTGACAACTTTATGACAG GGGATGCA).

These oligonucleotides provide a consensus *E. coli* pho box and −35 promoter region to generate a promoter that is potentially regulated by the phosphate concentration in the medium.

pMSXTp$_{13}$AB$_5$kan2 was constructed to provide expression of AB$_5$ from a promoter that has been shown to be expressed under general stress conditions such as nutrient limitation, pH or heat shock, and administration of toxic chemicals. The promoter region of uspA was aplified using oligonucleotides UspUp (SEQ ID NO:13)
(5' TGACCAACATACGA GCGGC)

and UspDwn (SEQ ID NO:14)
(5' CTACCAGAACTTTGCTTTCC)

in a PCR reaction consisting of an incubation at 95° C. for 3 min. followed by 30 cycles of 40 s at 95° C., 40 s at 42° C., an incubation for 7 min. at 68° C., and final storage at 4° C. The approximately 350 bp PCR product was cloned into pCR2.1 (Invitrogen Corp., USA) to generate pMBXp$_{13}$. An approximately 190 bp HincII-MscI fragment containing the promoter and transcriptional start site for uspA and the first 93 bp of the uspA mRNA was cloned into blunt ended BamHI-Sse8387I pMSXTp$_1$kan2 to give pMSXTp$_{13}$kan2. Plasmid pMSXTp$_{13}$kan2 was then KpnI digested, blunt ended with T4 polymerase and dephosphorylated using calf intestinal phosphatase. The AB$_5$ genes were isolated as a 2.0 kb EcoRI/Sse8387I fragment from pMSXAB$_5$, blunt ended using Klenow and T4 polymerase and ligated into the KpnI site of pMSXTp$_{13}$kan2. In the resulting plasmid pMSXTp$_{13}$AB$_5$kan2, the phbAB and kan genes are expressed from the uspA (p$_{13}$) promoter.

The p$_n$AB$_5$kan (n=11, 12, 13) expression cassettes were then excised as 2.8 kb AvrII fragments and ligated into the AvrII site of pUTHg and transformed into *E. coli* strain CC118 λpir to obtain plasmid pMUXp$_n$AB$_5$kan. This plasmid was then transformed into *E. coli* S17-1λpir and used to insert p$_{11}$AB$_5$kan, p$_{12}$AB$_5$kan, and p$_{13}$AB$_5$kan expression cassettes into the chromosome of *E. coli* strains by conjugation.

Example 6

Integration of C$_5$cat into the Chromosome of *E. coli*

C$_5$cat was introduced into the chromosome of MBX23 by conjugation using S17-1 λpir (pMUXC$_5$cat) as the donor strain. The conjugation mixture was spread on LB/N1/Cm plates and integrants were obtained, 40% of which were sensitive to ampicillin, indicating that no plasmid was present in these strains. Five integrants were transformed with pMSXAB$_5$cat (Ap$^r$) and grown on LB/Ap/Cm/2% glucose to examine biosynthetic activity of PHB polymerase (Table 4).

TABLE 4

Integrated Strains

| strain | strain containing pMSXAB5cat | PHB phenotype | strain after plasmid curing |
|---|---|---|---|
| MBX300 | MBX305 | ++++ | MBX325 |
| MBX301 | MBX308 | +++ | MBX331 |
| MBX302 | MBX310 | ++++ | MBX326 |
| MBX303 | MBX315 | ++++ | MBX327 |
| MBX304 | MBX316 | + | MBX337 |

Example 7

Amplification of C5 Expression in Integrated Strains

Expression of PHB polymerase was increased by restreaking MBX326 successively on LB plates containing 100, 200, 500, and 1000 µg/ml chloramphenicol. Strain MBX379 was derived from MBX326 and exhibited chloramphenicol resistance up to 1000 µg/ml. In Southern blot analysis of chromosomal DNA isolated from MBX379 and its predecessors, the phbC5 copy-number had not increased. Western blot analysis indicated a strong increase in PHB polymerase levels in cell free extracts of these strains when the phbAB genes were present on a plasmid.

Example 8

Integration of p$_{11}$AB$_5$kan, p$_{12}$AB$_5$kan and p$_{13}$AB$_5$kan into MBX379

S17-1 λpir strains with either pMUXp$_{11}$AB$_5$kan, pMUXp$_{12}$AB$_5$kan, or pMUXp$_{13}$AB$_5$kan were mated with MBX379. Transgenic strains in which phbAB$_5$kan had integrated on the chromosome were selected on LB/N1/Km plates. Among the integrants, PHB producers were identified on LB/glucose plates. Representatives of the individual constructs were MBX612 (MBX379::p$_{11}$AB$_5$kan), MBX677 (MBX379:: p$_{12}$AB$_5$kan), and MBX680 (MBX379::p$_{13}$AB$_5$kan). Southern blots and Western blots showed that the phbAB genes had integrated in the chromosome and were expressed in these strains as well. Table 5 shows the PHB accumulation levels of transgenic *E. coli* PHB producers grown in Luria-Bertani medium with 2% glucose or minimal E2 medium with 2% glucose and 0.5% corn steep liquor.

TABLE 5

PHB Accumulation Levels for Transgenic *E. coli* PHB Producers

| | % PHB of cell dry weight | |
|---|---|---|
| strain | LB/glucose | E2 glucose |
| MBX612 | 56 | 35 |
| MBX677 | 58 | 38 |
| MBX680 | 39 | 50 |

Example 9

Selection and Bacteriophage P1 Transduction to Yield Improved Strains

The growth characteristics of MBX612, 677, and 680 were improved by bacteriophage P1 transduction. A single transduction step was required to transduce the C₅cat and AB₅kan alleles from the different strains into LS5218, indicating that the two separate integration cassettes were located close to each other on the chromosome. The resulting strains are MBX690 (from MBX681), MBX691 (from MBX677), and MBX698 (from MBX680). Repeated inoculation of MBX612 on minimal E2 medium with limiting nitrogen resulted in MBX681. Unlike the strains generated by P1 transduction, MBX681 did not exhibit improved growth characteristics. Southern blots and Western blots show that phbC and the phbAB genes were successfully transduced and were expressed in these strains as well. Table 6 below shows PHB accumulation levels for these transgenic *E. coli* PHB producers grown in Luria-Bertani medium with 2% glucose or minimal E2 medium with 2% glucose and 0.5% corn steep liquor.

TABLE 6

PHB Accumulation Levels for Transgenic *E. coli* PHB Producers

| strain | % PHB of cell dry weight | |
|---|---|---|
| | LB/glucose | E2 glucose |
| MBX681 | 54 | 22 |
| MBX690 | 52 | 44 |
| MBX691 | 54 | 28 |
| MBX698 | 37 | 15 |

Example 10

Further Improvements of Transgenic *E. coli* Strains for PHB Production

Mutagenesis using NTG or EMS was used to further improve PHB production in MBX680. Strains MBX769 and MBX777 were selected after treatment of MBX680 with EMS and NTG, respectively. These strains were found to be able to grow on R2-medium supplied with 1% glucose, 0.5% corn steep liquor, and 1 mg/ml chloroamphenicol. MBX769 was grown in 50 ml R-10 medium/0.5% CSL with 2 or 3% glucose at 37° C. for 20 to 26 hours. PHB was accumulated to 71% of the cell dry weight. Similarly, MBX769 was grown in 50 ml LB with or without 0.375 g/L $KH_2PO_4$, 0.875 $K_2HPO_4$, 0.25 $(NH_4)_2SO_4$, and a total of 50 g/L glucose (five aliquots were added over the course of the incubation). After 63 hours of incubation, PHB had accumulated up to 96% of the cell dry weight.

The phbC and phbAB alleles from MBX777 were subsequently transduced into LS5218, resulting in MBX820. Southern blots and Western blots show that phbC and the phbAB genes were successfully transduced and were expressed in these strains as well. Table 7 shows the PHB accumulation levels of these transgenic *E. coli* PHB producers grown in Luria-Bertani medium with 2% glucose or minimal E2 medium with 2% glucose and 0.5% corn steep liquor.

TABLE 7

PHB Accumulation Levels for Transgenic *E. coli* PHB Producers

| strain | % PHB of cell dry weight | |
|---|---|---|
| | LB/glucose | E2 glucose |
| MBX680 | 39 | 50 |
| MBX777 | 67 | 57 |
| MBX820 | 53 | 50 |

Example 11

Growth Characteristics of Transgenic *E. coli* PHB Producers

The introduction of phb genes into MBX245 ($t_d$=47 min.) was accompanied by a reduction in growth rate (MBX680, $t_d$=71 min.). Improved PHB production was achieved by EMS mutagenesis, but did not improve the growth rate (MBX777, $t_d$=72 min.). P1 transduction of the PHB genes into a wild-type strain (MBX184) resulted in the same high growth rate as exhibited by MBX245 and PHB accumulation up to 50% of the cell dry weight in less than 24 hours (MBX820, $t_d$=45 min.).

Example 12

Plasmids for Chromosomal Integration of Other pha Genes

The integration of phbC, phbA, and phbB from *Z. ramigera* described herein also is applicable to other pha genes, such as genes encoding PHB polymerase from *R. eutroph* (C1), PHA polymerase from *P. oleovorans* (C3), PHB polymerase from *A. caviae* (C12), ACP ::CoA transacylase from *P. pulida* (G3), (R)-specific enouyl-CoA hydratase from *A. caviae* (J12), a broad substrate specific 3-ketoacyl-CoA thiolase from *R. eutropha* (A1-II), or a phasin from *R. eutropha* (P1-I and P1-II). These genes were obtained by polymerase chain reaction amplification using the following primers:

C1 up (SEQ ID NO:22)

5' g-GAATTC-aggaggtttt-ATGGCGACCGGCAAAGGCGCGGCAG 3'

C1 dw (SEQ ID NO:23)

5' GC-TCTAGA-AGCTT-tcatgccttggctttgacgtatcgc 3'

C3 up (SEQ ID NO:24)

5' g-GAATTC-aggaggtttt-ATGAGTAACAAGAACAACGATGAGC 3'

C3 dw (SEQ ID NO:25)

5' GC-TCTAGA-AGCTT-tcaacgctcgtgaacgtaggtgccc 3'.

C12 up (SEQ ID NO:26)

5' g-GAATTC-aggaggtttt-ATGAGCCAACCATCTTATGGCCCGC 3'

C12 dw (SEQ ID NO:27)

5' GC-TCTAGA-AGCTT-TCATGCGGCGTCCTCCTCTGTTGGG 3'

G3 up (SEQ ID NO:28)

5' g-GAATTC-aggaggtttt-ATGAGGCCAGAAATCGCTGTACTTG 3'

G3 dw (SEQ ID NO:29)

5' GC-TCTAGA-AGCTT-tcagatggcaaatgcatgctgcccc 3'

J12 up (SEQ ID NO:30)

5' ag-GAGCTC-aggaggtttt-ATGAGCGCACAATCCCTGGAAGTAG 3'

J12 dw (SEQ ID NO:31)

5' GC-TCTAGA-AGCTT-ttaaggcagcttgaccacggcttcc 3'

A1-II up (SEQ ID NO:32)

5' g-GAATTC-aggaggtttt-ATGACGCGTGAAGTGGTAGTGGTAAG 3'

```
-continued

A1-II dw
                                            (SEQ ID NO:33)
5' GC-TCTAGA-AGCTT-tcagatacgctcgaagatggcggc 3'.

P1-I up
                                            (SEQ ID NO:34)
5' g-GAATTC-aggaggtttt-
ATGATCCTCACCCCGGAACAAGTTG 3'

P1-I dw
                                            (SEQ ID NO:35)
5' GC-TCTAGA-AGCTT-tcagggcactaccttcatcgttggc 3'

P1-II up
                                            (SEQ ID NO:34)
5' g-GAATTC-aggaggtttt-
ATGATCCTCACCCCGGAACAAGTTG 3'

P1-II dw
                                            (SEQ ID NO:35)
5' GC-TCTAGA-AGCTT-tcaggcagccgtcgtcttctttgcc 3'
```

PCR reactions included 10 pmol of each primer, 1–5 µl of chromosomal DNA or boiled cells, and 45 µl PCRmix from Gibco BRL (Gaithersburg, Md.). Amplification was by 30 cycles of 60 s incubation at 94° C., 60 s incubation at a temperature between 45° C. and 68° C. and 1 to 3 minutes incubation at 72° C. PCR products were purified, digested with EcoRI and HindIII, blunt ended with the Klenow fragment of DNA polymerase, and cloned in the SmaI site of pMSXcat, pMSXkan, pMNXcat, or pMNXkan according to the schemes shown in FIGS. 1A–1C, 2A and 2B, and 3A–3C. pMUXpha was derived from pUTHg or pUTkan; and pMLXpha was derived from pLOFHg, where pha stands for the pha gene of choice. These plasmids were used for integration of the desired pha gene into the chromosome of E. coli or any other Gram-negative microbial strain suitable for PHA production.

Example 13

PHBV Copolymer Producing Transgenic E. coli Strains

E. coli strains with chromosomally integrated phb genes such as described above also can be used to produce PHBV copolymers. PHBV is generally synthesized in fermentation systems where propionic acid is co-fed with glucose or other carbohydrate. After uptake, propionate is converted to propionyl-CoA, which by the action of acyl-CoA thiolase and 3-ketoacyl-CoA reductase is converted to 3-hydroxyvaleryl-CoA (3HV-CoA). 3HV-CoA is subsequently polymerized by PHA polymerase.

The capacity to accumulate PHBV can be increased by increasing levels of enzymes that specifically synthesize HV monomers. Such enzymes may be involved in the uptake of propionic acid, in the activation of propionic acid to propionyl-CoA or in any of the PHB biosynthetic enzymes. Additionally, alternative enzymes can be isolated from other sources, or propionyl-CoA can be obtained from alternative pathways, e.g. from the methylmalonyl-CoA pathway. In this pathway, succinyl-CoA is converted to methylmalonyl-CoA which is then decarboxylated to yield propionyl-CoA.

Example 14

PHB-4HB Copolymer Producing Transgenic E. coli Strains

Homopolymers and copolymers containing 4HB monomers can be produced by transgenic E. coli strains. Incorporation of 4HB from 4HB-CoA can be achieved by feeding 4-hydroxybutyrate to the PHA producing organisms. 4HB is activated to 4HB-CoA either through a 4-hydroxybutyryl-CoA transferase such as hbcT (OrfZ) from Clostridium kluyveri or by an endogenous E. coli enzyme or by any other enzyme with this capability. A P4HB homopolymer is produced when the transgenic E. coli strain contains only the phbC gene. 4HB containing copolymers can be synthesized when the transgenic E. coli strain contains genes encoding the complete PHB biosynthetic pathway.

E. coli MBX821 (LS5218::$C_5$-cat$^{379}$, atoC$^c$) was grown in Luria-Bertani medium and resuspended in 100 ml 10% LB with 5 g/L 4HB and 2 g/L glucose. After incubation of this culture for 24 hours, PHA was characterized and identified as containing only 4HB monomers. Similarly, E. coli MBX777 with a plasmid containing hbcT such as pFS16, was grown in LB/4HB (5 g/L) and the resuting polymer was identified as PHB4HB with 35.5% 4HB monomers.

Example 15

Production of poly(4-hydroxybutyrate) from 4-hydroxybutyrate in Recombinant E. coli with No Extrachromosomal DNA Poly(4-hydroxybutyrate) can be synthesized from 4-hydroxybutyrate by E. coli expressing 4-hydroxybutyryl-CoA transferase (hbcT) and PHA synthase (phaC) genes from a plasmid. If these genes are integrated into the E. coli chromosome and expressed at high levels, the recombinant E. coli should be able to synthesize poly(4-hydroxybutyrate) from 4-hydroxybutyrate. The hbcT and phbC genes were inserted into pUTHg (Herrero, et al., J. Bacteriol. 172:6557–67, 1990) as follows. pMSXC$_5$cat and pFS16 were both digested with BamHI and SalI. The large fragment of pMSXC$_5$cat and the fragment of pFS16 containing the hbcT gene thus obtained were ligated together using T4 DNA ligase to form pMSXC$_5$hbcT-cat. The fragment containing the phaC, hbcT, and cat genes was removed from pMSXC$_5$hbcT-cat by digestion with AvrII, and it was inserted using T4 DNA ligase into pUTHg that had been digested with AvrII and treated with calf intestinal alkaline phosphatase to prevent self-ligation. The plasmid thus obtained was denoted pMUXC$_5$hbcT-cat. The plasmid pMUXC$_5$hbcT-cat was replicated in MBX129 and conjugated into MBX1177. The strain MBX1177 is a spontaneous mutant of E. coli strain DH5α that was selected for its ability to grow on minimal 4-hydroxybutyrate agar plates. MBX1177 is also naturally resistant to nalidixic acid. The recipient cells were separated from the donor cells by plating on LB-agar supplemented with 25 µg/mL chloramphenicol and 30 µg/mL nalidixic acid. Survivors from this plate were restreaked on minimal medium, containing, per liter: 15 g agar; 2.5 g/L LB powder (Difco; Detroit, Mich.); 5 g glucose; 10 g 4-hydroxybutyrate; 1 mmol MgSO$_4$; 10 mg thiamine; 0.23 g proline; 25.5 mmol Na$_2$HPO$_4$; 33.3 mmol K$_2$HPO$_4$; 27.2 mmol KH$_2$PO$_4$; 2.78 mg FeSO$_4$.7H$_2$O; 1.98 mg MnCl$_2$.4H$_2$O; 2.81 mg CoSO$_4$.7H$_2$O; 0.17 mg CuCl$_2$.2H$_2$O; 1.67 mg CaCl$_2$.2H$_2$O; 0.29 mg ZnSO$_4$.7H$_2$O; and 0.5 mg chloramphenicol. Colonies from this plate that appeared to be especially white and opaque were evaluated in shake flasks containing the same medium as above except without agar. The individual colonies were first grown in 3 mL of LB medium for 8 hours, and 0.5 mL of each culture was used to inoculate 50 mL of the medium described above. These flasks were incubated at 30° C. for 96 hours. One isolate was found by GC analysis (for which the cells were removed from the medium by centrifugation for 10 minutes at 2000×g, washed once with water and centrifuged again, then lyophilized) to contain 4.9% poly(4-hydroxybutate) by weight. This strain was denoted MBX1462 and selected for further manipulations. MBX1462 was treated with the mutagen 1-methyl-3-nitro-1-nitrosoguanidine (MNNG), a chemical mutagen, by exposing a liquid culture of MBX1462 to 0.1 mg/mL MNNG for 90 minutes. It was found that 99.8% of the cells were killed by this treatment. The plating and shake flask experiment described above was repeated, and one isolate was found by GC analysis to contain 11% poly(4-hydroxybutate) by weight. This strain was denoted MBX1476 and selected for further manipulations. The NTG treatment was repeated and killed 96.3% of the cells. The plating and shake flask experiment described above was repeated once again, and one isolate was found by GC analysis to contain 19% poly(4-hydroxybutate) by weight. This strain was denoted MBX1509.

Example 15

PHBH Copolymer Producing Transgenic *E. coli* Strains

*E. coli* MBX240 is an XL1-blue (Stratagene, San Diego, Calif.) derivative with a chromosomally integrated copy of the PHB polymerase encoding phbC gene from *Ralstonia eutropha*. This strain does not form PHAs from carbon sources such as glucose or fatty acids, because of the absence of enzymes converting acetyl-CoA (generated from carbohydrates such as glucose) or fatty acid oxidation intermediates, into (R)-3-hydroxyacyl-CoA monomers for polymerization. pMSXJ12 was constructed by inserting the phaJ gene from *A. caviae* digested with EcoR1 and PstI into the corresponding sites of pUC18Sfi. The phaJ gene was obtained by polymerase chain reaction using the primers Ac3–5:

```
Ac3-5':
                                          (SEQ ID NO:37)
5' AGAATTCAGGAGGACGCCGCATGAGCGCACAATCCCTGG and Ac3-3':
                                          (SEQ ID NO:38)
5' TTCCTGCAGCTCAAGGCAGCTTGACCACG
``` using a PCR program including 30 cycles of 45 s at 95° C., 45 s at 55° C. and 2.5 minute at 72° C. Transformants of *E. coli* MBX240 with plasmid pMTXJ12 containing the (R)-specific enoyl-CoA hydratase encoded by the phaJ gene from *Aeromonas caviae* were grown on Luria-Bertani medium with 10 mM octanoate and 1 mM oleate. After 48 hours of growth, cells were harvested from a 50 ml culture by centrifugation and the cell pellet lyophilized. Lyophilized cells were extracted with chloroform (8 ml) for 16 hours and PHA was specifically precipitated from the chloroform solution by adding the chloroform layer to a 10-fold excess ethanol. Precipitation was allowed to occur at 4° C. and the solid polymer was air dried and analyzed for composition by acidic butanolysis. Butylated PHA monomers were separated by gas chromatography and identified the PHA as a poly(3-hydroxybutyrate-co-3-hydroxyhexanoate) copolymer with 2.6% 3-hydroxyhexanoate monomers.

Example 16

Construction of Transgenic *E. coli* Strains for Screening of New and/or Improved Genes for PHA Production The phbC gene was introduced into an *E. coli* cloning strain by bacteriophage P1 transduction. In a procedure similar to that followed for phbC$_5$ integration, the phbC gene from *R. eutropha* was integrated into the chromosome of MBX23, resulting in MBX143. After chloramphenicol amplification, MBX150, which is resistant to 500 μg/ml chloramphenicol, was isolated. A bacteriophage P1 lysate grown on MBX150 was used to transduce the phbC-cat allele into XL1-Blue [pT7-RecA]. Plasmid pT7RecA expresses a functional RecA protein which is required for successful P1 transduction. The resulting strain MBX240 is an XL1-Blue derivative with a functional PHB polymerase expressed from the chromosome. MBX613 and MBX683 were developed using the same procedures. These strains were derived from MBX245 and XL1-Blue, respectively, and contain integrated AB$_5$cat (MBX613) or p$_{13}$AB$_5$kan (MBX683) operons.

Example 17

Identification of Genes Encoding New, Improved or Ancillary PHA Biosynthetic Enzymes MBX240, 613, and 683 are three strains that can be used in screening procedures for new or improved PHA genes. Using these strains, the following genes have been identified: phbCABFA2 from *P. acidophila* and phbCAB from *A. latus*. In addition, the phaJ gene from *A. caviae* was functionally expressed in MBX240 to produce PHA from fatty acids. Besides PHA biosynthetic genes specific for $C_3$ to $C_6$ monomers, PHA biosynthetic enzymes for PHAs consisting of medium side-chain 3-hydroxy acids can also be expressed in *E. coli*. Such strains are useful in identifying additional PHA biosynthetic enzymes.

Example 18

Integration of pha Genes in *R. eutropha*

The plasmids described in the previous examples were used to integrate pha genes in *R. eutropha*. Using a PHA-negative mutant of *R. eutropha* such as #2 (Peoples & Sinskey, *J. Biol. Chem.* 264:15298–303 (1989)) or PHB-4 (Schubert, et al., *J. Bacteriol.* 170:5837–47 (1988)), PHA formation was restored by integration of phaC from *A. caviae* in combination with phbAB from *Z. ramigera* or phaJ from *A. caviae*. The resulting strains produced PHAs to variable levels, with a molecular weight in the range of 400,000 to 10,000,000 Da and with a composition that includes monomers such as 3-hydroxyhexanoate and 3-hydroxyoctanoate.

Example 19

Integration of pha Genes in *P. putida*

The plasmids described in the previous examples were used to integrate pha genes into *Pseudomonas putida*. The PHA-negative phenotype of *P. putida* GPp104 (Huisman et al., *J. Biol. Chem.* 266:2191–98 (1991)) was restored by integration of a phaC3kan cassette where phaC3 encodes the PHA polymerase from *P. oleovorans*. Integration of phaC3kan using pMUXC3kan was also applied to generate mutants of *P. putida* with mutations in genes encoding enzymes that affect PHA metabolism other than phaC. The PHA polymerase gene from *A. caviae* was also introduced in to the chromosome to result in a strain that produces PHAs including 3-hydroxy fatty acids in the $C_3$ to $C_9$ range.

Example 20

Chromosomal Integration of phaC Genes to Control Molecular Weight of the Resulting PHA It is well known that the concentration of PHA polymerase determines the molecular weight of the produced PHA when substrate is available in excess. Variation of the molecular weight is desirable as polymer properties are dependent on molecular weight. Chromosomal integration of phb genes results in variable levels of expression of the pha gene as determined by the chromosomal integration site. It is therefore possible to obtain different transgenic bacteria that have variable levels of phaC expression and hence produce PHAs of variable molecular weight. With this system, it is possible to produce PHAs with molecular weights of greater than 400,000 Da and frequently even in excess of 1,000,000 Da. This procedure is applicable to any gram-negative bacterium in which the pUT or pLOF derived plasmids can be introduced, such as *E. coli, R. eutropha, P. putida, Klebsiella pneumoniae, Alcaligenes latus, Azotobacter vinelandii, Burkholderia cepacia, Paracoccus denitrificans* and in general in species of the *Escherichia, Pseudomonas, Ralstonia, Burkholderia, Alcaligenes, Klebsiella, Azotobacter* genera.

Example 21

Integration of the PHB Genes as a Single Operon

A plasmid, pMSXABC$_5$kan, was constructed such that the thiolase (phbA), reductase (phbB), and PHB synthase (phbC) genes from *Zoogloea ramigera* and the kanamycin resistance gene (kan) were linked as an operon in the vector pUC18Sfi. This expression cassette was then excised as an AvrII fragment and inserted into the AvrII site of pUT to obtain pMUXABC$_5$kan.

S17-1 λpir strains with pMUXABC$_5$kan were mated with MBX247. Transgenic strains in which phbABC$_5$kan had integrated into the chromosome were selected on LB/N1/Km plates. Among the integrants, PHB producers were identified on LB/glucose plates. One strain thus constructed, MBX1164, was selected for further study.

Thiolase (Nishimura et al., 1978, Arch. Microbiol. 116:21–24) and reductase (Saito et al., 1977, Arch. Microbiol. 114:211–217) assays were conducted on MBX1164 crude extracts. The cultures were grown in 50 mL of 0.5×E2 medium supplemented with 20 g/L glucose. One unit (U) was defined as the amount of enzyme that converted 1 82 mol of substrate to product per min. 3-Ketothiolase activity was determined to be 2.23±0.38 and 2.48±0.50 U/mg in two independent trials, and 3-hydroxybutyryl-CoA reductase activity was determined to be 4.10±1.51 and 3.87±0.15 U/mg in two independent trials.

Strain MBX1164 was evaluated for its PHB-producing ability in square shake bottles. The cells were grown in 2 mL of LB, and 0.1 mL of this was used as an inoculum for the 50-mL shake bottle culture. The shake bottle contained E2 medium supplemented with 0.25% corn steep liquor (Sigma, St. Louis, Mo.) and 20 g/L glucose. After incubation at 30° C. for 48 hours with shaking at 200 rpm, the biomass concentration had reached 2.6 g/L, and the PHB concentration had reached 11.7 g/L; thus the cells contained 82% PHB by weight.

Example 22

Integration of the *Pseudomonas oleovorans* PHA Synthase into the *E. coli* Chromosome A PHA synthase (phaC) cassette from the *P. oleovorans* chromosome and a promoterless chloramphenicol resistance gene were inserted into pUC118 such that an operon of the two genes was formed; i.e., they were oriented in the same direction and could be transcribed on the same mRNA. The sequence of the *P. oleovorans* phaC gene is shown below. The phaC-cat operon was excised from this plasmid by digestion with KpnI and HindIII and ligated to pUC18SfiI that had been digested with the same two enzymes to form pMSXC$_3$cat. This allowed the phaC-cat operon to be flanked by AvrII sites. The phaC-cat operon was removed from pMSXC$_3$cat by digestion with AvrII and FspI. Because the two AvrII fragments of pMSXC$_3$cat were nearly the same size, FspI was used to facilitate isolation of the phaC-cat operon by cutting the rest of the vector into two pieces. The AvrII fragment was ligated to pUTkan which had been digested with AvrII and treated with alkaline phosphatase to prevent self-ligation. The plasmid thus produced was denoted pMUXC$_3$cat. The operon on this plasmid actually consisted of phaC-cat-kan. Strain CC118 λpir (a λpir lysogenic strain) was transformed with pMUXC$_3$cat to produce strain MBX130. Equal amounts of strains MBX130 and MBX245 were mixed on an LB agar plate and incubated for 8 hours at 37° C. The mixed cells were then used as an inoculum for an overnight 37° C. culture of LB-chloramphenicol (25 μg/mL)-nalidixic acid (30 μg/mL). Single colonies were isolated from this culture by plating on LB-chloramphenicol (25 μg/mL)-nalidixic acid (30 μg/mL)-kanamycin (25 μg/mL). The colonies thus isolated have a transducible phaC-cat-kan cassette on the chromosome, as shown by the ability to use P1 transduction to introduce the cassette into the chromosome of other strains and select for resistance to both chloramphenicol and kanamycin.

```
Pseudomonas oleovorans PHA synthase (phaC).

(SEQ ID NO:39)
ATGAGTAACAAGAACAACGATGAGCTGCAGCGGCAGGCCTCGGAAAACACCCTGGGGCTGAACCCGGTCATC

GGTATCCGCCGCAAAGACCTGTTGAGCTCGGCACGCACCGTGCTGCGCCAGGCCGTGCGCCAACCGCTGCAC

AGCGCCAAGCATGTGGCCCACTTTGGCCTGGAGCTGAAGAACGTGCTGCTGGGCAAGTCCAGCCTTGCCCCG

GAAAGCGACGACCGTCGCTTCAATGACCCGGCATGGAGCAACAACCCACTTTACCGCCGCTACCTGCAAACC

TATCTGGCCTGGCGCAAGGAGCTGCAGGACTGGATCGGCAACAGCGACCTGTCGCCCCAGGACATCAGCCGC

GGCCAGTTCGTCATCAACCTGATGACCGAAGCCATGGCTCCGACCAACACCCTGTCCAACCCGGCAGCAGTC

AAACGCTTCTTCGAAACCGGCGGCAAGAGCCTGCTCGATGGCCTGTCCAACCTGGCCAAGGACCTGGTCAAC

AACGGTGGCATGCCCAGCCAGGTGAACATGGACGCCTTCGAGGTGGGCAAGAACCTGGGCACCAGTGAAGGC
```

| Pseudomonas oleovorans PHA synthase (phaC). |
|---|
| GCCGTGGTGTACCGCAACGATGTGCTGGAGCTGATCCAGTACAACCCCATCACCGAGCAGGTGCATGCCCGC |
| CCGCTGCTGGTGGTGCCGCCGCAGATCAACAAGTTCTACGTATTCGACCTGAGCCCGGAAAAGAGCCTGGCA |
| CGCTACTGCCTGCGCTCGCAGCAGCAGACCTTCATCATCAGCTGGCGCAACCCGACCAAAGCCCAGCGCGAA |
| TGGGGCCTGTCCACCTACATCGACGCGCTCAAGGAGGCGGTCGACGCGGTGCTGGCGATTACCGGCAGCAAG |
| GACCTGAACATGCTCGGTGCCTGCTCCGGCGGCATCACCTGCACGGCATTGGTCGGCCACTATGCCGCCCTC |
| GGCGAAAACAAGGTCAATGCCCTGACCCTGCTGGTCAGCGTGCTGGACACCACCATGGACAACCAGGTCGCC |
| CTGTTCGTCGACGAGCAGACTTTGGAGGCCGCCAAGCGCCACTCCTACCAGGCCGGTGTGCTCGAAGGCAGC |
| GAGATGGCCAAGGTGTTCGCCTGGATGCGCCCCAACGACCTGATCTGGAACTACTGGGTCAACAACTACCTG |
| CTCGGCAACGAGCCGCCGGTGTTCGACATCCTGTTCTGGAACAACGACACCACGCGCCTGCCGGCCGCCTTC |
| CACGGCGACCTGATCGAAATGTTCAAGAGCAACCCGCTGACCCGCCCGGACGCCCTGGAGGTTTGCGGCACT |
| CCGATCGACCTGAAACAGGTCAAATGCGACATCTACAGCCTTGCCGGCACCAACGACCACATCACCCCGTGG |
| CAGTCATGCTACCGCTCGGCGCACCTGTTCGGCGGCAAGATCGAGTTCGTGCTGTCCAACAGCGGCCACATC |
| CAGAGCATCCTCAACCCGCCAGGCAACCCCAAGGCGCGCTTCATGACCGGTGCCGATCGCCCGGGTGACCCG |
| GTGGCCTGGCAGGAAAACGCCACCAAGCATGCCGACTCCTGGTGGCTGCACTGGCAAAGCTGGCTGGGCGAG |
| CGTGCCGGCGAGCTGAAAAAGGCGCCGACCCGCCTGGGCAACCGTGCCTATGCCGCTGGCGAGGCATCCCCG |
| GGCACCTACGTTCACGAGCGTTGA |

Modifications and variations of the present invention will be obvious to those of skill in the art from the foregoing detailed description. Such modifications and variations are intended to come within the scope of the following claims.

We claim:

1. A genetically engineered microorganism producing polyhydroxyalkanoate, the improvement comprising having at least one heterologous bacterial gene encoding enzyme involved in the synthesis of polyhydroxalkanoates selected from the group consisting of thiolase, reductase, PHB synthase, PHA synthase, acyl-CoA transferase, and enoyl-CoA hydratase integrated into the chromosome, which stably expresses the enzyme and thereby has enhanced production of polyhydroxyalkanoate.

2. The microorganism of claim 1 selected from the group consisting of *E. coil, Azotobacter, Pseudomonas putida,* and *Ralstonia eutropha(Alcaligenes eutrophus)*.

3. The microorganism of claim 1 wherein the heterologous bacterial gene is inserted using transposon delivery.

4. The microorganism of claim 1 comprising multiple integrated bacterial genes expresing enzymes involved in synthesis of polyhydroxyalkcanoate wherein the integrated genes are operably linked as an operon.

5. The microorganism of claim 1 wherein the integrated bacterial gene is operably linked under the control of a promoter.

6. The microorganism of claim 1 wherein the integrated bacterial gene is operably linked with upstream activating sequences.

7. The microorganism of claim 1 wherein the integrated bacterial gene is operably linked with mRNA stabilizing sequences.

8. The microorganism of claim 5 wherein the promoter includes a consensus *E. coil* pho box and −35 promoter region that is regulated by the phosphate concentration in the medium.

9. The microorganism of claim 5 wherein the promoter is selected from the group consisting of a promoter that induces expression under general stress conditions such as nutrient limitation, pH or heat shock, and administration of toxic chemicals.

10. The microorganism of claim 1 wherein the integrated bacterial gene is operably linked with a selection marker.

11. The microorganism of claim 1 wherein the integrated bacterial gene is isolated or derived from a microorganism selected from the group consisting of *A. eutrophus, Aeromonas caviae, Zoogleoa ramigera, Nocardia, Rhodococcus, Pseudomonas* Sp. 6-3, *Pseudomonas acidophila, Pseudomonas oleovarans, Chromobacterium violaeuum,* and *Alcaligenes latus*.

12. The microorganism of claim 1 wherein the integrated bacterial gene encodes an enzyme selected from the group consisting of PHB polymerase from *R. eutropha* (C1), PHA polymerase from *P. oleovorans* (C3), PHB polymerase from *A. caviae* (C12), ACP::CoA transacylase from *P. putida* (G3), (R)-specific enouyl-CoA hydratase from *A. caviae* (J12), a broad substrate specific 3-ketoacyl-CoA thilase from *R. eutropha* (A1-II), and phasins from *R. eutropha* (P1-I and P1-II).

13. The microorganism of claim 1 wherein the bacterial gene is integrated as a single copy on the chromosome of the microorganism.

14. A method for screening for a bacterial gene involved in synthesis of polyhydroxyalkanoates that enhances production comprising mutating a genetically engineered microorganism having at least one bacterial gene encoding an enzyme involved in synthesis of polyhydroxyalkanoates selected from group consisting of thiolase, reductase, PHB synthase, PHA synthase, acyl-CoA transferase enoyl-CoA hydratase, wherein the gene is integrated into the chromosome, which stably expresses the enzyme so that the microorganism produces polyhydroxyalkanoate, and screening for enhanced production of polyhydroxyalkanoates relative to pro duction of polyhydroxyalkanoate by the microorganism expressing the enzyme from a gene which is not integrated, by measuring the increase in the percent by weight of the polhydyroxyalkanoate.

15. The method of claim 14 wherein the integrated bacterial gene is isolated or derived from a microorganism selected from the group consisting of *A. eutrophus, Aeromonas caviae, Zoogloea ramigera, Nocardia, Rhodococcus, Pseudomonas* Sp. 61-3, *Pseudomonas acidophila, Pseudomonas oleovarans, Chromobacterium violaceum,* and *Alcaligenes latus*.

16. A method for producing polyhydroxyalkanoates comprising culturing genetically engineered microorganisms capable of producing polyhydroxyalkanoates having at least one bacterial gene encoding an enzyme involved in synthesis of polyhydroxyalkanoates selected from the group consisting of thiolase, reductas, PHB synthase, PHA synthase, acyl-CoA transferase, enoyl-CoA hydratase, integrated into the chromosome, with appropriate substrate under condi tions wherein the microorganisms produce polyhydroxyalkanoate.

17. The method of claim 16 wherein the microorganisms comprise multiple integrated bacterial genes involved in synthesis of polyhydroxyalkanoate wherein the integrated genes are operably linked as an operon.

18. The method of claim 16 wherein the microorganisms comprise bacterial genes selected from the group consisting of genes integrated operably linked under the control of a promoter, genes integrated and operably linked with upstream activating sequences, genes integrated and operably linked with mRNA stabilizing sequences, genes operably linked with a promoter including a consensus *E. coli* pho box and −35 promoter region that is regulated by the phosphate concentration in the medium, and genes integrated and operably linked with a selection marker.

\* \* \* \* \*

UNITED STATES PATENT AND TRADEMARK OFFICE
CERTIFICATE OF CORRECTION

PATENT NO. : 6,913,911 B2
APPLICATION NO. : 10/461069
DATED : July 5, 2005
INVENTOR(S) : Gjalt W. Huisman, Oliver P. Peoples and Frank A. Skraly It is certified that error appears in the above-identified patent and that said Letters Patent is hereby corrected as shown below:

Column 2, line 63, "ph-stat" should be replaced with --pH-stat--.
Column 5, line 26, "mutiple" should be replaced with --multiple--.
Column 5, line 54, "demonstratd" should be replaced with --demonstrated--
Column 6, line 23, "polyhydroxylkanoates" should be replaced with --polyhydroxyalkanoates--.
Column 6, line 65 "stabilzed" should be replaced with --stabilized--.
Column 7, line 45, "endogeneous" should be replaced with --endogenous--.
Column 8, line 19, "*Chromotium*" should be replaced with --*Chromatium*--.
Column 8, line 52-53, please delete "*A. latus*"
Column 10, line 66, "homogy" should be replaced with --homology--.
Column 11, line 30, "prefered" should be replaced with --preferred--.
Column 11, line 36, "prefered" should be replaced with --preferred--.
Column 13, line 44, "containing 30 g/ml" should be replaced with --containing 30 μg/ml--.
Column 13, line 46, "containing 50 g/ml" should be replaced with --containing 50 μg/ml--.
Column 14, line 60, "DNa" should be replaced with --DNA--.
Column 15, line 26, "polyrmerase" should be replaced with --polymerase--.
Column 20, line 19, "enouyl" should be replaced with --enoyl--.
Column 22, line 17, "resuling" should be replaced with-- resulting--.
Claim 1, column 41, line 36, please insert --an-- between "encoding" and "enzyme".
Claim 2, column 41, line 43, "E. coil" should be replaced with --*E. coli*--.
Claim 2, column 41, line 43, please insert the term --*Alcaligenase latus*-- between "*E. coli*" and "*Azotobacter*"
Claim 4, column 41, line 48, "expresing" should be replaced with --expressing--.
Claim 4, column 41, line 49, "polyhydroxyalkcanoate" should be replaced with --polyhydroxyalkanoate--.
Claim 8, column 41, line 59, "E. coli pho" should be replaced with --*E. coli pho*--.
Claim 11, column 42, line 39, "Sp." should be replaced with --*Sp.*--.
Claim 12, column 42, line 47, "enouyl-CoA" should be replaced with --enoyl-CoA--.
Claim 12, column 42, line 48, "thilase" should be replaced with --thiolase--.
Claim 14, column 43, line 4, "polhydroxyalkanoate" should be replaced with --polyhydroxyalkanoate--.
Claim 15, column 43, line 9, "Sp." should be replaced with --*Sp.*--.
Claim 16, column 43, line 17, "reductas" should be replaced with --reductase--.
Claim 16, column 43, line 14, please delete "capable of producing polyhydroxyalkanoates".

UNITED STATES PATENT AND TRADEMARK OFFICE
CERTIFICATE OF CORRECTION

PATENT NO.       : 6,913,911 B2
APPLICATION NO.  : 10/461069
DATED            : July 5, 2005
INVENTOR(S)      : Gjalt W. Huisman, Oliver P. Peoples and Frank A. Skraly It is certified that error appears in the above-identified patent and that said Letters Patent is hereby corrected as shown below:

Claim 18, column 44, line 3, please insert --and-- between "integrated" and "operably".
Claim 18, column 44, line 9, please insert --and-- between "integrated" and "operably".
Claim 18, column 44, line 15, "pho" should be replaced with -- *pho*--.

Signed and Sealed this

Twelfth Day of December, 2006

JON W. DUDAS
*Director of the United States Patent and Trademark Office*